(12) United States Patent
Nieman et al.

(10) Patent No.: US 10,945,756 B2
(45) Date of Patent: Mar. 16, 2021

(54) DEVICE OF INSERTING AND CONTROLLING A SNARE

(71) Applicant: Catch Medical, LLC, Salt Lake City, UT (US)

(72) Inventors: Timothy Nieman, North Salt Lake, UT (US); Tab Robbins, Salt Lake City, UT (US); Collin George Cowley, Salt Lake City, UT (US)

(73) Assignee: Catch Medical, LLC, Salt Lake City, UT (US)

( * ) Notice: Subject to any disclaimer, the term of this patent is extended or adjusted under 35 U.S.C. 154(b) by 0 days.

(21) Appl. No.: 13/782,564

(22) Filed: Mar. 1, 2013

(65) Prior Publication Data
US 2014/0249540 A1 Sep. 4, 2014

(51) Int. Cl.
*A61B 17/3205* (2006.01)
*A61B 17/221* (2006.01)
(Continued)

(52) U.S. Cl.
CPC ...... *A61B 17/32056* (2013.01); *A61B 17/221* (2013.01); *A61B 2017/0053* (2013.01); *A61B 2017/00358* (2013.01); *A61B 2017/00469* (2013.01); *A61B 2017/2212* (2013.01); *A61B 2017/22035* (2013.01)

(58) Field of Classification Search
CPC ............ A61B 17/221; A61B 17/32056; A61B 2017/2212; A61B 2017/2215; A61B 2017/2217; A61B 2017/00358; A61B 2017/00469; A61B 2017/22035; A61B 17/0485; A61B 17/06109; A61B 2018/1407; A61B 2018/141; A61M 25/01; A61M 25/0102; A61M 25/0113; A61M 25/0147; A61M 2025/015; A61M 25/013; A61M 25/09041; A61M 2025/09116; A61M 25/09; A61M 25/0105; A61M 25/0163; A61M 2025/09125; Y10T 24/3936; Y10T 24/3938; Y10T 24/3953;
(Continued)

(56) References Cited

U.S. PATENT DOCUMENTS 3,312,128 A * 4/1967 Wasson ................. E04G 21/122
81/487
3,628,221 A * 12/1971 Pasbrig .................. A44B 11/16
226/147
(Continued)

OTHER PUBLICATIONS

Merriam-Webster online dictionary definition of rivet (https://www.merriam-webster.com/dictionary/rivet). Accessed via wayback machine (Apr. 21, 2009).*
(Continued)

*Primary Examiner* — Katherine H Schwiker
(74) *Attorney, Agent, or Firm* — Stoel Rives LLP

(57) ABSTRACT

Embodiments of the present invention relate to systems, methods, and apparatus for introducing and/or controlling a snare in a lumen (e.g., a lumen of a catheter tube, a body lumen, etc.). In one example, a snare loading device can reduce the size of a loop on a snare to allow the snare to be inserted into the catheter tube. Furthermore, before and/or after insertion of the snare into the catheter tube, the snare loading device can control the snare, by transferring motion thereto.

14 Claims, 15 Drawing Sheets

(51) Int. Cl.
*A61B 17/00* (2006.01)
*A61B 17/22* (2006.01)

(58) Field of Classification Search
CPC ............ Y10T 24/3951; Y10T 24/3969; Y10T 24/3996; A61F 2002/9517
USPC ................ 606/113, 114, 127, 108, 128, 103; 600/585
See application file for complete search history.

(56) References Cited

U.S. PATENT DOCUMENTS

| | | | |
|---|---|---|---|
| 4,278,042 A * | 7/1981 | Lindquist | B63B 21/08 |
| | | | 114/218 |
| 4,878,270 A * | 11/1989 | Westerkamp | F16G 11/04 |
| | | | 24/132 R |
| 4,886,067 A | 12/1989 | Palermo | |
| 4,912,817 A * | 4/1990 | Sandreid | F16G 11/10 |
| | | | 24/132 R |
| 5,137,288 A * | 8/1992 | Starkey | A61M 25/09 |
| | | | 279/42 |
| 5,159,861 A * | 11/1992 | Anderson | A61B 17/22 |
| | | | 226/127 |
| 5,171,314 A * | 12/1992 | Dulebohn | A61B 17/32056 |
| | | | 606/110 |
| 5,325,868 A * | 7/1994 | Kimmelstiel | A61B 17/22 |
| | | | 600/585 |
| 5,399,165 A * | 3/1995 | Paul, Jr. | A61M 25/0147 |
| | | | 604/174 |
| 5,417,684 A | 5/1995 | Jackson et al. | |
| 5,431,370 A * | 7/1995 | Verkuylen | H02G 1/085 |
| | | | 254/134.3 FT |
| 5,486,182 A | 1/1996 | Nakao et al. | |
| 5,562,678 A | 10/1996 | Booker | |
| 5,653,009 A * | 8/1997 | Kassardjian | A44C 5/2061 |
| | | | 24/616 |
| 5,906,621 A | 5/1999 | Secrest | |
| 6,007,546 A | 12/1999 | Snow et al. | |
| 6,126,654 A | 10/2000 | Giba et al. | |
| 6,533,772 B1 * | 3/2003 | Sherts | A61M 25/0113 |
| | | | 279/42 |
| 7,029,488 B2 * | 4/2006 | Schonholz et al. | 606/200 |
| 7,052,489 B2 | 5/2006 | Griego et al. | |
| 8,133,252 B2 | 3/2012 | Davis et al. | |
| 8,690,891 B2 | 4/2014 | Cowley et al. | |
| 2003/0109874 A1 | 6/2003 | Dennis | |
| 2003/0135222 A1 | 7/2003 | Baska | |
| 2005/0038424 A1 | 2/2005 | Okada | |
| 2005/0043743 A1 | 2/2005 | Dennis | |
| 2005/0124912 A1 | 6/2005 | Griego et al. | |
| 2005/0277962 A1 | 12/2005 | Myers | |
| 2006/0173468 A1 | 8/2006 | Simmon et al. | |
| 2007/0016224 A1 | 1/2007 | Nakao | |
| 2007/0112359 A1 | 5/2007 | Kimura et al. | |
| 2009/0163896 A1 * | 6/2009 | Kumate | A61B 17/32056 |
| | | | 606/1 |
| 2011/0077621 A1 * | 3/2011 | Graham | A61M 25/0097 |
| | | | 604/528 |
| 2011/0087247 A1 | 4/2011 | Fung et al. | |
| 2011/0238147 A1 * | 9/2011 | Bennett et al. | 623/1.11 |
| 2012/0004647 A1 | 1/2012 | Cowley | |
| 2012/0011906 A1 * | 1/2012 | Wildauer et al. | 70/182 |
| 2013/0261610 A1 * | 10/2013 | LaConte | A61B 17/2909 |
| | | | 606/1 |

OTHER PUBLICATIONS

International Search Report and Written Opinion dated Feb. 22, 2012 for PCT/US2011/042448.
Office Action dated Jan. 8, 2013 for U.S. Appl. No. 12/862,347.
Office Action dated Jul. 3, 2013 for U.S. Appl. No. 12/830,060.
Office Action dated Jul. 15, 2013 for U.S. Appl. No. 12/862,347.
Office Action dated Oct. 17, 2012 for U.S. Appl. No. 12/830,060.
European Search Report dated May 11, 2018 for EP11801367.1.

* cited by examiner

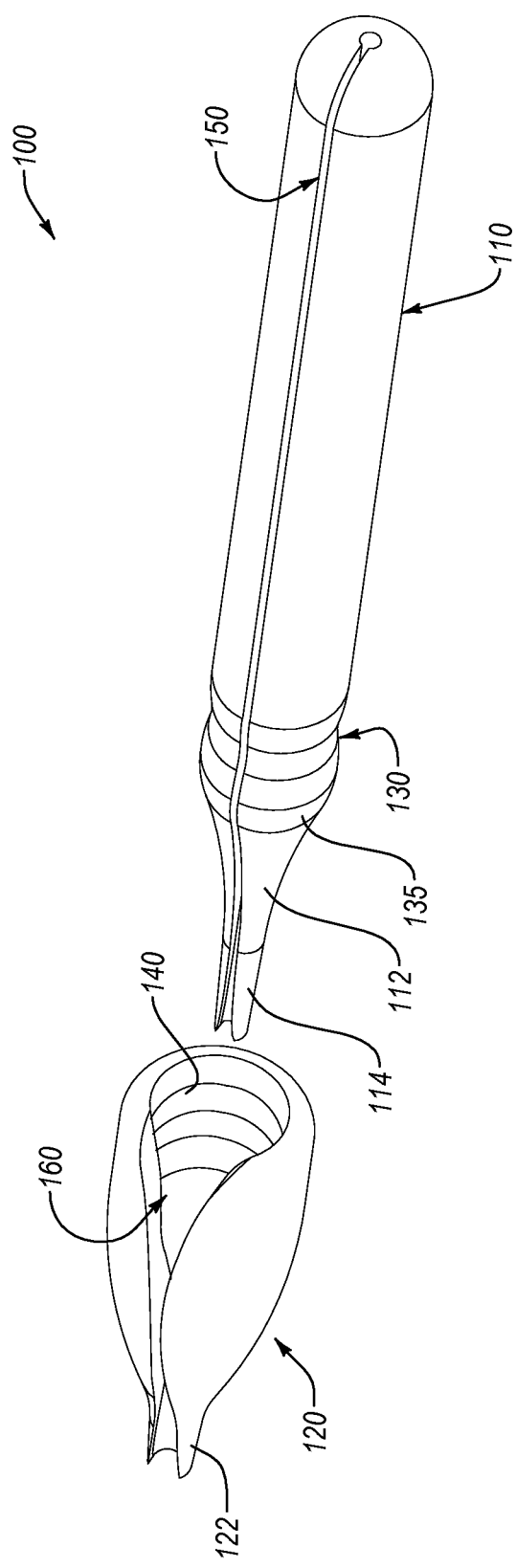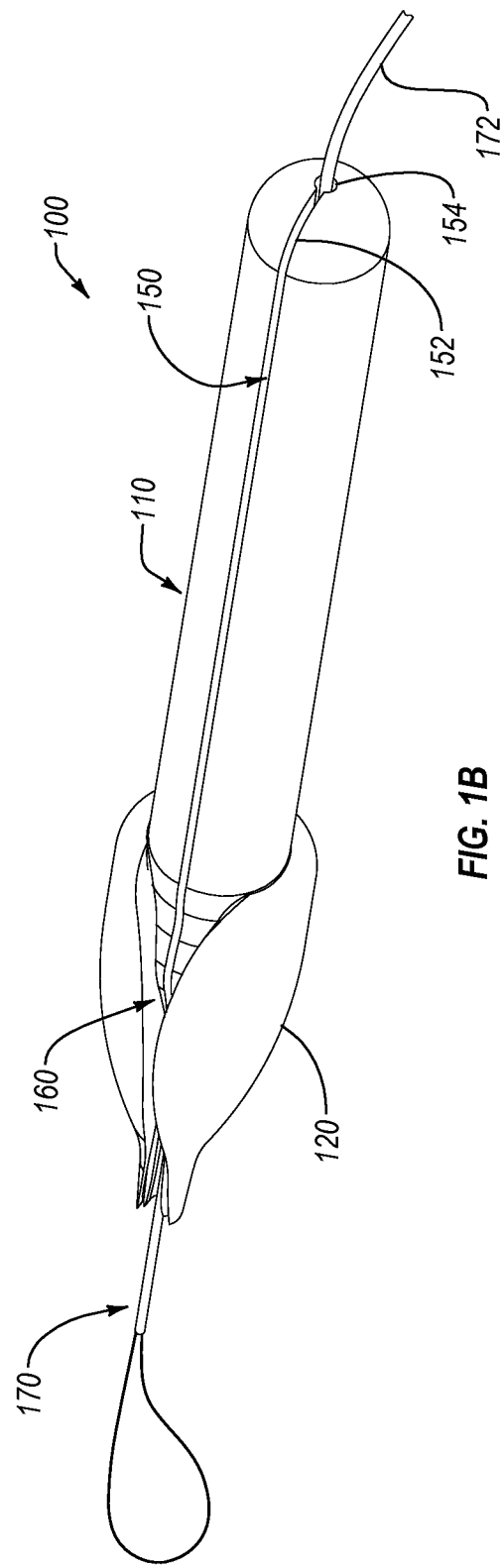

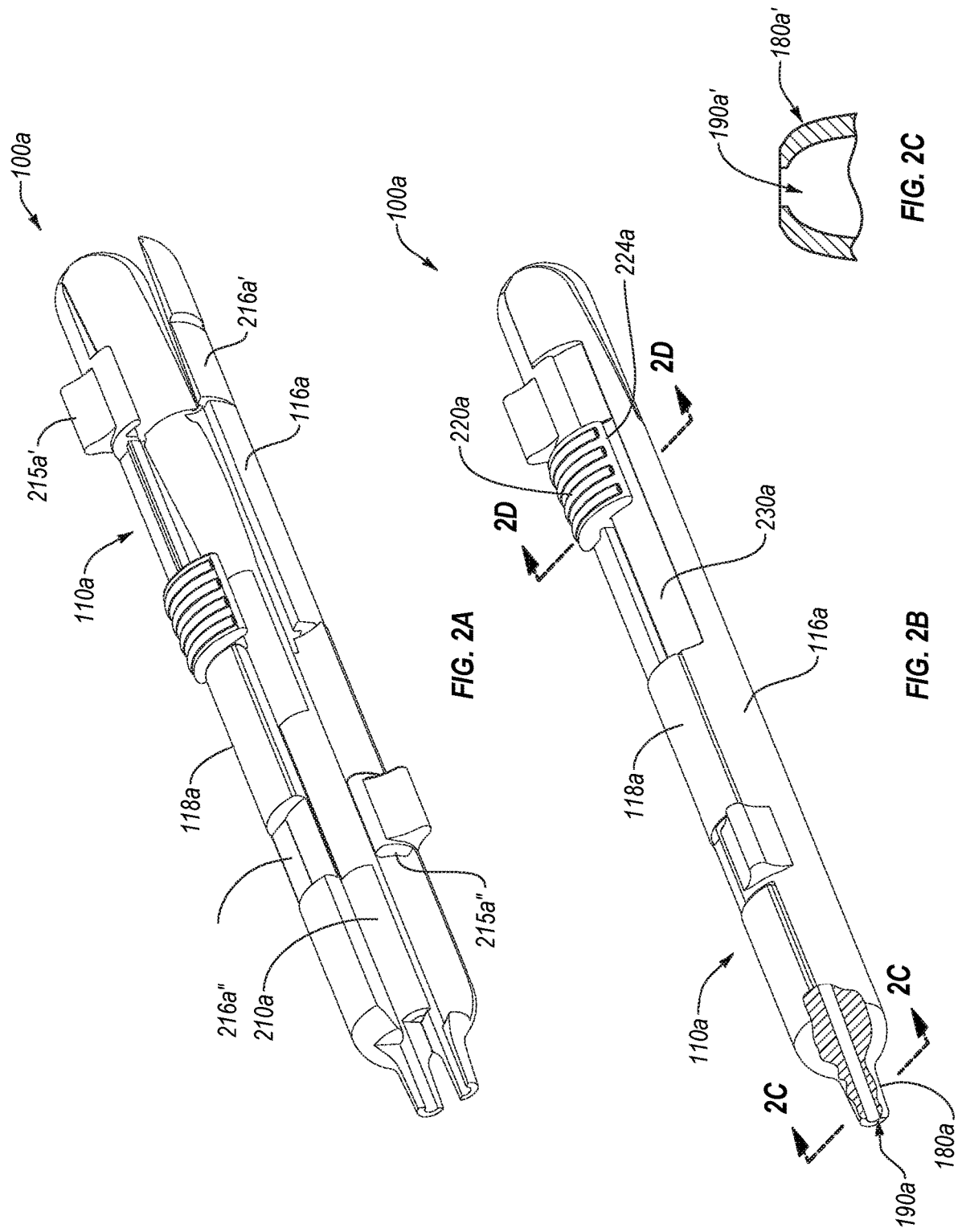

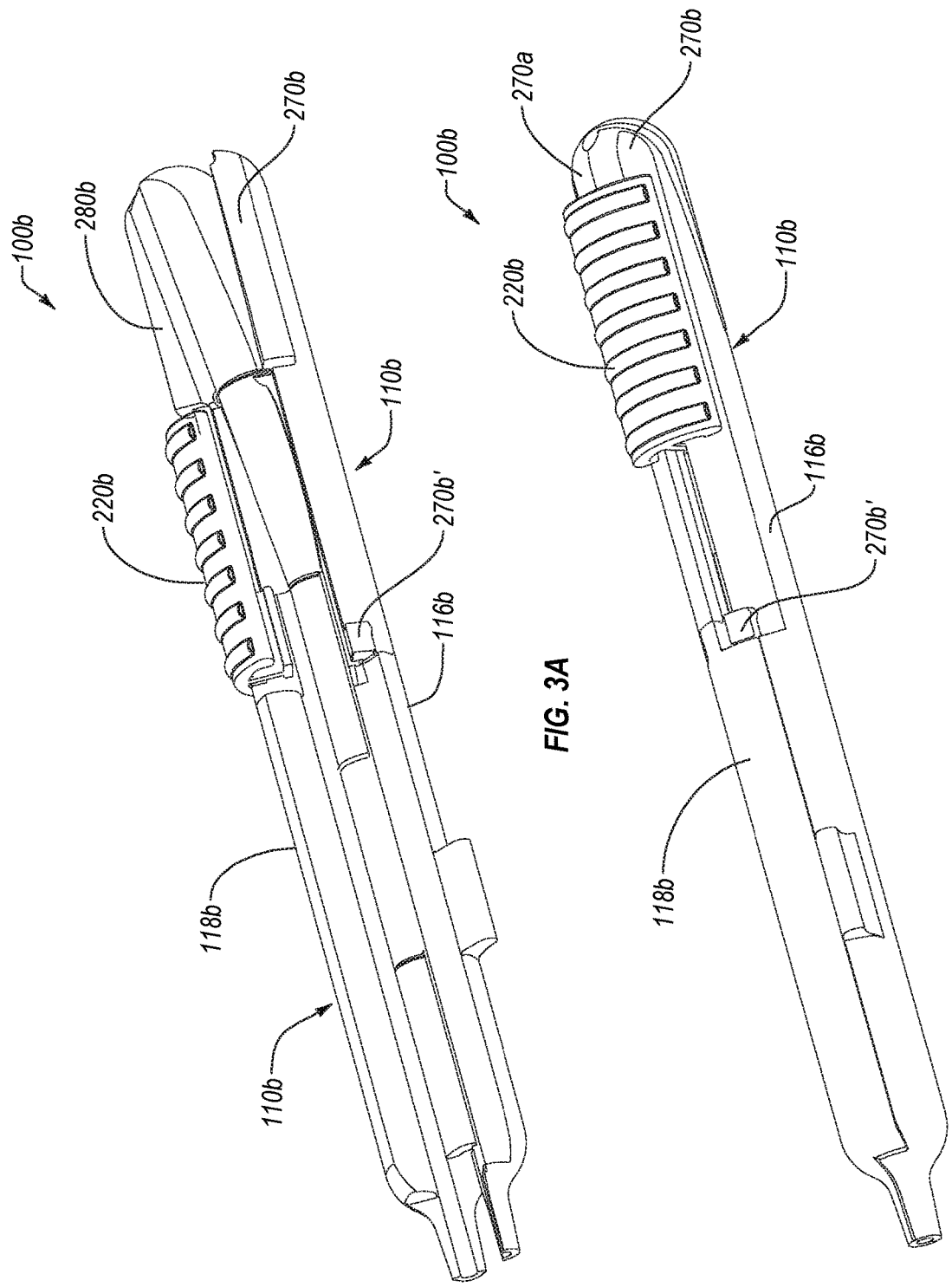

DEVICE OF INSERTING AND CONTROLLING A SNARE

BACKGROUND OF THE INVENTION

1. The Field of the Invention

This invention relates to systems, methods, and apparatus for inserting and/or controlling a medical snare in a lumen.

2. Background and Relevant Art

Common surgical and endovascular techniques make use of guide wires, catheters, stents, and other medical devices that may be placed within the body lumens of a patient. Such medical devices may occasionally break or fragment during installation, use, or retraction, thereby releasing all or a portion of the device into the patient's vascular system or other body lumens. In still other surgical procedures, sponges, gauze, or other medical materials may be inserted into an organ or vascular space, and left behind after surgery.

Medical devices or materials that fragment, break or are inadvertently left behind in surgery are foreign to the body. In many circumstances, such foreign bodies may need to be removed due to failure or dislocation, or for the patient's safety, health, or well-being. For instance, a foreign body may dislodge and move through the bloodstream and potentially contribute to thrombosis, sepsis, arrhythmia, or a number of other complications. Accordingly, when an undesired foreign body is detected within a patient's organs or vasculature, it is typically desirable to remove the foreign body from the patient.

To remove the foreign body, a surgeon may resort to an open surgical technique; however, open surgery is often expensive, time consuming, and traumatic to the patient. Open surgery will often require longer healing times and result in greater risks of complications when compared to other, less invasive techniques. The risk of complication can increase if the patient has recently undergone another surgical procedure.

Alternatively, the foreign body can be removed with a medical snare device. For instance, the snare can have a loop on the end thereof, which can capture the foreign body. Particularly, the snare can be inserted into the body lumen, capture the foreign body, and together with the foreign body be retracted from the body lumen.

In order to introduce the snare into the body lumen the open loop of the wire can be compressed and oriented, such as to align it and allow it to enter the lumen where it can expand and can fill the lumen space available. Typically, snares currently in existence consist of a loop or loops on a distal end of a simple wire. Therefore, loading and advancement of the snare into a lumen may be accomplished by advancing a cylindrical loading mechanism from the proximal end of the snare's wire, over the wire until the cylindrical shape compresses the loop and orients it by compression into a more axially compressed condition.

Once compressed, the snare loop can be advanced into the lumen, and the loading mechanism can be removed axially from the proximal end of the device. Further, to rotationally and axially grip and control the snare, a locking mechanism, typically of collet type structure, can be advanced from the proximal end of the snare and, then, actuated to grip the wire. As such, multiple devices may be required to load and lock the snare.

In some instances, various mechanisms can be attached to the proximal end of these wires and devices. Such mechanisms can impede or prevent advancement or removal of loading mechanisms and/or locking mechanisms onto the snare wire from the proximal end thereof. Accordingly, a need exists for a mechanism or mechanisms for the loading, locking, and/or combined loading and locking of a snare.

BRIEF SUMMARY

Embodiments of the present invention provide systems, methods, and apparatus for introducing and/or controlling a snare in a lumen (e.g., a lumen of a catheter tube, an introducer sleeve, a body lumen, etc.). More specifically, a snare loading device can be utilized to reduce the size of and direct the end of a loop, which can be located on a distal end of the snare in preparation for introduction into some lumen or entrance. Such reduction and orientation of the loop can be sufficient to allow the snare to be inserted into the lumen. Furthermore, before and/or after insertion of the snare into the lumen, the snare loading device can control the snare, by transferring motion thereto (e.g., by gripping fixedly or by providing a channel through which the snare may be axially advanced or retracted).

At least one embodiment includes a snare loading device. Particularly, the snare loading device can have a main body and a main channel located in the main body. The main channel can be defined by and between a left half and a right half of the main body, which can form the channel when in the halves are in contact. Furthermore, the main channel can be sized and configured to accept and compress the loop of the snare and/or a wire of a snare. The snare loading device also can include an aperture in a distal end of the main body. The aperture can be formed by the main channel passing through the distal end of the main body. The aperture also can be configured to compress or further compress a loop of the snare. Moreover, the snare loading device can include a nose piece having a secondary channel sized and configured to allow the wire of the snare to pass therethrough. The nose piece can be rotatably coupled to the main body in a manner that the nose piece can rotate to align the secondary channel with the main channel. Additionally, the nose piece can be rotatable to close the main channel.

Additional or alternative embodiments can include another snare loading device. Such snare loading device can have a main body having a left half rotatably secured to a right half and a main channel located in the main body. The main channel can be defined by and between the left half and the right half of the main body when the halves are in contact with each other. Additionally, the main channel can be sized and configured to accept and or compress the loop or a wire of a snare. The main channel also can provide an aperture at a distal end of the main body. Such aperture can be configured to compress or further compress a loop of the snare. Furthermore, the snare loading device can incorporate a lock slidably secured to the main body. The lock can have a lower portion thereof configured to clamp the wire of the snare in the main channel fixedly locating the snare axially within the loading device.

Embodiments also can include yet another snare loading device. Such snare loading device can have a left half of a main body having a substantially flat inside surface and a right half of the main body having a substantially flat inside surface. The right half can be rotatably secured to the left half. Furthermore, the snare loading device can have a main channel defined between the left half and the right half when the main body is in a closed configuration. The snare loading device also can include a lock slidably coupled to one or more of the left half and the right half. The lock can have a lower portion sized and configured to clamp a wire of a snare in the main channel to fixedly locate the snare wire axially within the loading device.

Additional features and advantages of exemplary embodiments of the invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. Understanding that these drawings depict only typical embodiments of the invention and are not therefore to be considered to be limiting of its scope, the invention will be described and explained with additional specificity and detail through the use of the accompanying drawings in which:

FIG. 1A illustrates a perspective exploded view of a snare loading device in accordance with one embodiment of the present invention;

FIG. 1B illustrates a perspective assembled view of the snare loading device of FIG. 1A with an open channel and a snare inserted therein;

FIG. 2A illustrates a perspective view of a snare loading device in an open configuration in accordance with another embodiment of the present invention;

FIG. 2B illustrates a perspective view of the snare loading device of FIG. 2A in a closed configuration;

FIG. 2C illustrates a cross-section view of a tip of a snare loading device in accordance with one or more embodiments of the present invention;

FIG. 3A illustrates a perspective view of a snare loading device in an open configuration in accordance with yet another embodiment of the present invention;

FIG. 3B illustrates a perspective view of the snare loading device of FIG. 3A in a closed configuration;

DETAILED DESCRIPTION OF THE PREFERRED EMBODIMENTS

Figure 1C:
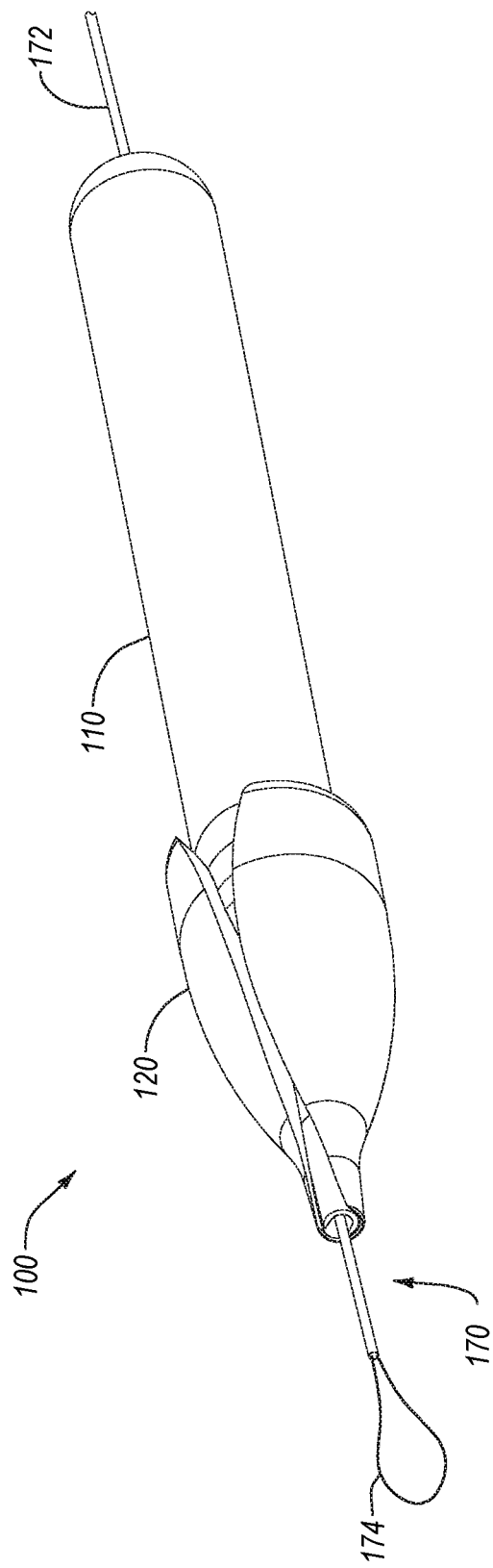
FIG. 1C illustrates a perspective view of the snare loading device of FIG. 1B with a closed main channel.

Embodiments of the present invention provide systems, methods, and apparatus for introducing and/or controlling a snare in a lumen (e.g., a lumen of a catheter tube, an introducer sleeve, a body lumen, etc.). More specifically, a snare loading device can be utilized to reduce the size of and direct the end of a loop, which can be located on a distal end of the snare in preparation for introduction into some lumen or entrance. Such reduction and orientation of the loop can be sufficient to allow the snare to be inserted into the lumen. Furthermore, before and/or after insertion of the snare into the lumen, the snare loading device can control the snare, by transferring motion thereto (e.g., by gripping fixedly or by providing a channel through which the snare may be axially advanced or retracted).

Additionally, the snare loading device can laterally engage the snare at any portion thereof throughout the axial length of the snare. In other words, loading a proximal end of the snare into the snare loading device and pulling the snare through the snare loading device can be avoided. Likewise passing the distal end of the snare through the loading device can also be avoided. Hence, in one example, the snare loading device can engage the snare near the loop, such that the loop can be forced into the snare loading device, which can reduce the loop sufficiently to fit into the lumen. Accordingly, the snare loading device can allow a user to quickly insert the snare into the lumen (e.g., into a lumen of a catheter tube), preventing the need for axial passage of the snare device through the loading device, which can reduce the total time required for retrieving the foreign object and can reduce the risk and/or harmful effects related to the presence of the foreign object in the body.

Furthermore, the snare loading device can releasably and selectively clamp onto the snare. As such, the snare loading device can transfer rotational and axial motion and control the snare in the catheter tube as well as in the body lumen. Particularly, the snare loading device can transmit radial and/or axial motion to the snare. Consequently, the snare loading device can facilitate rotation of the snare to a desired position (e.g., in close proximity to or over the foreign body to be withdrawn).

Likewise, the snare loading device can advance or move the snare forward (in the distal direction) and can retract or move the snare backward (in the proximal direction). In some embodiments, the snare loading device also can prevent unwanted or inadvertent forward movement of the snare. For instance, the snare loading device can be clamped to the snare, while distal end of the snare loading device can remain stationary, thereby preventing forward movement of the snare. In some embodiments, the snare loading device can be inserted into and fixed relative to the catheter tube and/or into a luer connected to the catheter tube, thus fixing the snare loop axially and/or rotationally with respect to the catheter lumen or foreign object. Alternatively, for instance, the snare loading device can abut the catheter tube or lumen directly. In any event, the snare loading device can manipulate the snare close to the foreign body so that the snare can capture the foreign body, and pull the snare together with the foreign body in the proximal direction.

In at least one embodiment, the snare loading device can have a slot or a channel that can span between opposing ends of the snare loading device, and which can accept a portion of the snare therein. For instance, an exemplary snare loading device 100 is illustrated in FIG. 1A. Particularly, the snare loading device 100 can include a main body 110 and a nose piece 120 that can be rotatably coupled or secured to the main body 110. The main body and nose piece having axial slots that when aligned can create a slot throughout the length of the snare loading device 100 and when rotationally misaligned close segments or portions of the slot in order to create an intact through lumen to capture and compress the snare wire or snare loop within the snare loading device 100.

Furthermore, the nose piece 120 can be selectively and removably coupled to the main body 110. For example, the main body 110 can have an undercutting section 130 that can receive a corresponding protruding section 140 of the nose piece 120. Moreover, the undercutting section 130 and the protruding section 140 can form a snap fit, such that the nose piece 120 can snap over the main body 110. Likewise, the fit between the undercutting section 130 and the protruding section 140 can be such that the nose piece 120 and the main body 110 can be separated or disengaged from each other. In other words, the nose piece 120 and main body 110 can be selectively coupled together and decoupled from each other.

To facilitate selective coupling between the nose piece 120 and the main body 110, the undercutting section 130 and protruding section 140 can have suitable configurations, which can vary from one embodiment to another. In at least one embodiment, the undercutting section 130 can have a rounded front edge 135. Accordingly, the rounded front edge of the undercutting section 130 can reduce the force required to couple and/or decouple the nose piece 120 from the main body 110. Additionally or alternatively, a portion of the protruding section 140 can be rounded, which also can reduce resistance to decoupling the nose piece 120 from the main body 110. In any event, the undercutting section 130 and the protruding section 140 can be configured in a manner that provides sufficient coupling strength between the main body 110 and the nose piece 120, while allowing the main body 110 to decouple from the nose piece 120 without damage.

As noted above, the nose piece 120 can be rotatably coupled to the main body 110. For instance, the main body 110 and the nose piece 120 can be free to rotate 360° relative to each other. To facilitate such rotation, while maintaining the main body 110 coupled to the nose piece 120, in some embodiments, the undercutting section 130 can encircle the main body 110, such that the protruding section 140 remains within the undercutting section 130 as the main body 110 and nose piece 120 rotate relative to each other. In additional or alternative embodiments, the protruding section 140 can encircle the nose piece 120, thereby allowing the protruding section 140 to remain within the undercutting section 130 during a 360° relative rotation of the main body 110 and the nose piece 120.

In light of this disclosure, those skilled in the art should appreciate that the main body 110 and nose piece 120 can have less than 360° freedom of relative rotation. Also, the undercutting section 130 and/or the protruding section 140 can span less the 360° about the respective main body 110 and nose piece 120. Furthermore, the main body 110 and/or the nose piece 120 can incorporate stops that can delimit the range of relative rotation of the main body 110 and nose piece 120, as may be desired for a particular use or application.

Additionally, as the nose piece 120 is coupled to the main body 110, a portion of the main body 110 can fit inside the nose piece 120. In one or more embodiments, the main body 110 can have a tapered distal portion 112 that can fit inside the nose piece 120. For instance, the tapered distal portion 112 of the main body 110 can have a snug fit inside the nose piece 120. Alternatively, however, the tapered distal portion 112 of the main body 110 can loosely fit inside the nose piece 120.

Also, a distal section 114 of the tapered distal portion 112 can fit inside a corresponding distal section 122 of the nose piece 120. In one example, the distal section 114 can have a snug, tight, or an interference fit inside the distal section 122. Thus, when the nose piece 120 is coupled to the main body 110, the distal section 114 can remain substantially fixed relative to the distal section 122.

As further described below, in one embodiment, the nose piece 120 can secure the snare within the snare loading device 100. More specifically, the main body 110 can have a main channel 150, which can span from a distal end to a proximal end of the main body 110. The nose piece 120 can have a secondary channel 160 that can span between the opposing ends of the nose piece 120. The main channel 150 and the secondary channel 160 can be sized and configured to accept at least a portion of the snare therein.

For example, the secondary channel 160 and the main channel 150 can be aligned in a manner that forms a substantially uniform, open channel and/or exposes the main channel 150 in the main body 110, as illustrated in FIG. 1B. In other words, the nose piece 120 and the main body 110 can be rotated relative to each other to align the secondary channel 160 with the main channel 150. Hence, the snare loading device 100 can receive a portion of a snare 170 in the main channel 150 of the main body 110. As noted above, the main channel 150 can span between the opposing distal and proximal ends of the main body 110. Furthermore, the main channel 150 can be configured such that the center line of the snare 170 approximately coincides with the centerline of the main body 110.

In some embodiments, the main channel 150 can have a narrow portion 152, which can be narrower than the outside dimension of the snare 170. In other words, the portion of the snare 170 that is to be received within the main channel 150 may have an interference with the narrow portion 152. Moreover, the main channel 150 can have a fitted portion 154 that can be configured to have substantially the same shape and size as the portion of the snare 170 received within the main body 110. In some instances, the portion of the snare 170 received in the main body 110 can be a wire snare 170 of the snare 170, which can have a particular diameter. Hence, the fitted portion 154 can have a cylindrical shape (i.e., a substantially circular cross-section) of substantially the same or similar diameter as a wire 172 of the snare 170.

Accordingly, the wire of the snare can be pushed through the narrow portion 152 and secured within the fitted portion 154 of the main channel 150. Furthermore, as noted above, the nose piece 120 and the main channel 150 can be rotatably coupled together. Hence, in additional or alternative embodiments, the nose piece 120 can be rotated relative to the main body 110, such as to close a portion of the main channel 150 located near the proximal end of the main body 110, as illustrated in FIG. 1C. In any event, the snare 170 can be secured within the main channel 150 of the main body 110, with a loop 174 of the snare 170 remaining outside of the snare loading device 100.

Figure 1D:
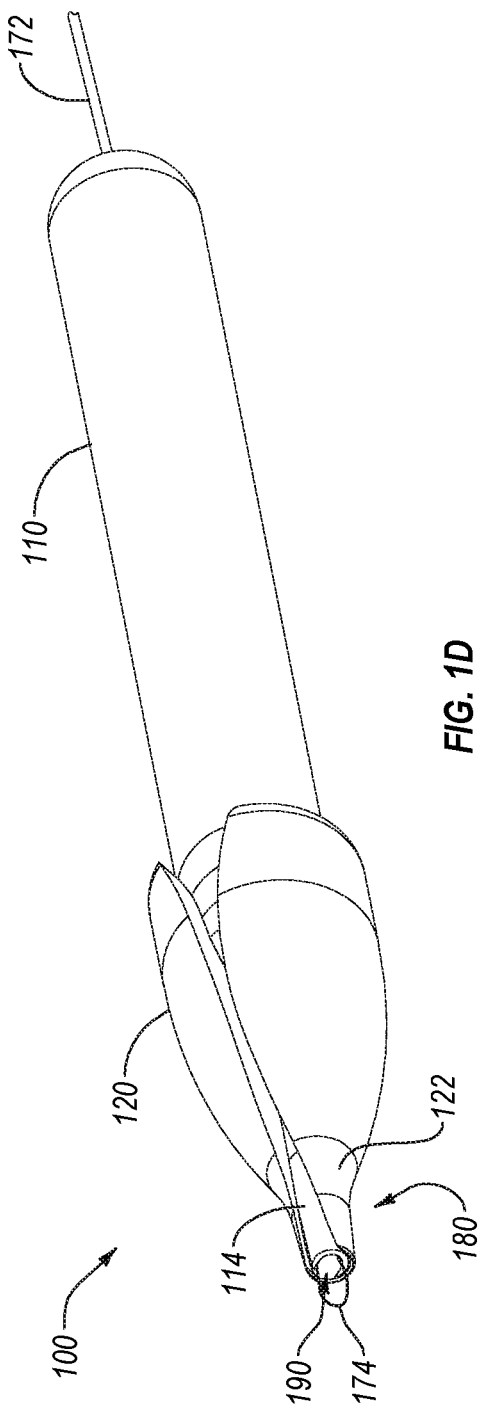
FIG. 1D illustrates a perspective view of the snare loading device of 1C with a collapsed loop of a snare.

Subsequently, as illustrated in FIG. 1D, the snare 170 can be pulled in the proximal direction thereby collapsing the loop 174 of the snare 170. As the snare is pulled (e.g., by pulling the wire 172) in the proximal direction, the loop 174 can be forced into a tip 180 of the snare loading device 100. In some embodiments, the tip 180 can be formed or defined by the distal ends of the nose piece 120 and main body 110. Particularly, the distal section 114 of the main body 110 and the distal section 122 of the nose piece 120 can form the tip 180.

The tip 180 can include an aperture 190 that can accept and reduce the loop 174, as the snare 170 is pulled in the distal direction (or as the snare loading device 100 moves proximally along the snare 170). In some examples, the aperture 190 can be defined by the main channel of the main body 110 and by a portion of the distal section 122 of the nose piece 120. In any event, the aperture 190 can have sufficient size and rigidity to compress the loop 174, as the loop 174 is forced into the aperture 190. Also, the distal section 122 of the nose piece 120 can provide additional strength and reinforcement to the distal section 114, thereby forming a sufficiently rigid aperture 190 that can compress the loop 174 to a desired size and configuration.

Figure 1E:
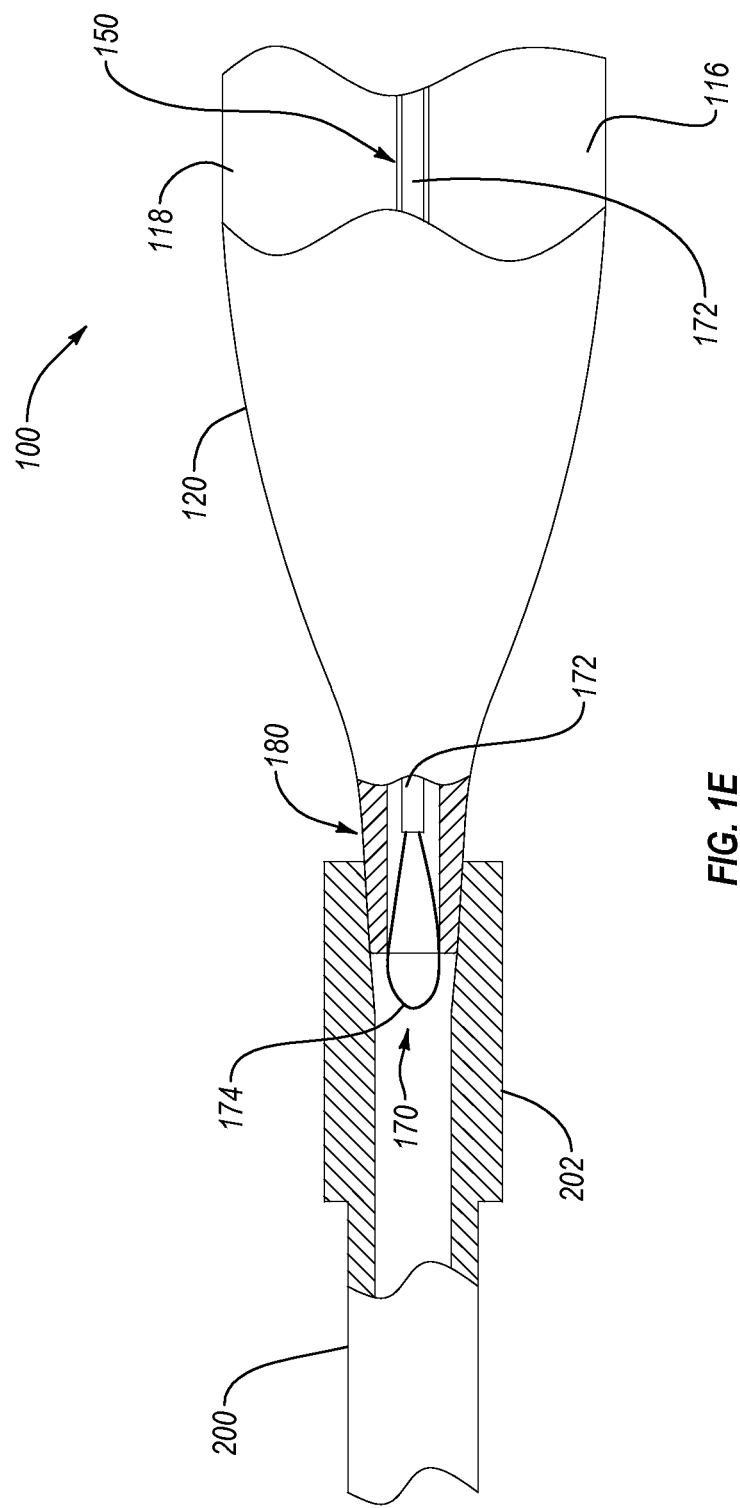
FIG. 1E illustrates a top view of the snare loading device of FIG. 1D coupled with a luer.

Once the loop 174 is reduced to a desired size and configuration (e.g., configured to substantially cylindrical outer limits), the snare 170 (including the loop 174) can be inserted into the catheter tube. For example, as illustrated in FIG. 1E, the tip 180 of the snare loading device 100 can be inserted into a catheter tube 200. In some instances, the catheter tube 200 can include a luer 202, which can accept and couple to the tip 180 of the snare loading device 100. Furthermore, the loop 174 of the snare 170 can be reduced to fit into the lumen of the luer 202 and into the catheter tube 200. Hence, the snare can slide into the catheter tube 200, for instance, when the wire 172 of the snare is advanced forward, through the snare loading device 100 and into the catheter tube 200.

Accordingly, the snare 170 can be advanced to or near a target site, for capturing the foreign body. It should be appreciated that as the snare 170 exits the snare loading device 100, in some embodiments, the loop 174 can expand to the size of the lumen of the catheter tube 200. Likewise, as the snare 170 exits the catheter tube 200, the loop can expand to a preloaded state thereof. Subsequently, the snare 170 can be controlled in a manner that can capture a foreign body with the loop 174 of the snare 170.

For example, as mentioned above, the snare loading device 100 also can be used to control the snare within a body lumen, vascular cavity, and the like. In one embodiment, the main channel 150 can be configured in a manner that pressure applied on opposing sides of the main channel 150 can reduce the size of the main channel 150 and clamp the snare 170 or a portion thereof (e.g., the wire 172) located within the main channel 150. Specifically, left and right halves 116, 118 of the main body 110 can be pressed toward each other, to reduce the size of the main channel 150. The main body 110 can have sufficient flexibility to allow the user to press together the left and right halves 116, 118, thereby clamping the wire 172. For instance, the main body 110 can comprise a thermoplastic material, such as nylon, polyethylene, polypropylene, etc., which can be configured to have sufficient flexibility, which can allow the user to compress the main channel 150 and clamp the wire 172 therein. Consequently, as the wire 172 is clamped in the main channel 150, the user can rotate the snare loading device 100 in a clockwise and/or counterclockwise direction, to transfer the rotational motion to the snare 170.

Moreover, the main body 110 can be configured such that, as the user reduces the amount of pressure applied to the left and/or right halves 116, 118 the main body 110 can return or flex back to the original or un-flexed configuration. In other words, the by reducing the pressure applied to the left and/or right halves 116, 118, the wire 172 can be released or unclamped from the snare loading device 100. Hence, the snare can be easily selectively clamped and unclamped in the snare loading device 100.

Thus, for instance, the wire 172 can be clamped in the snare loading device 100, and the snare loading device 100 can be rotated in a first direction. Because the wire 172 is clamped in the snare loading device 100, the snare 170 can be rotated together with the snare loading device 100. Thereafter, pressure about the opposing sides of the main channel 150 can be reduced, such as to unclamp the wire 172, and the snare loading device 100 can be rotated in a second direction, opposite to the first direction. As the snare 170 is unclamped from the snare loading device 100, the snare loading device 100 can rotate independently of the snare 170 (i.e., as the snare loading device 100 rotates, the snare 170 can remain substantially stationary).

In one embodiment, the nose piece 120 and the main body 110 can have a threaded connection, such that the nose piece 120 can be threaded onto the main body 110. Moreover, the corresponding threaded sections of the nose piece 120 and of the main body 110 can be tapered, in a manner that rotation and/or coupling of the nose piece 120 to the main body 110 can press the left and right halves 116, 118 together, thereby clamping the wire 172 in the main channel 150. Accordingly, the wire 172 can be safely secured within the main channel 150 by rotating the nose piece 120 relative to the main body 110.

Additionally, to ensure stationary positioning of the snare 170, the wire 172, which can protrude past the proximal end of the main body 110, can be held stationary as the snare loading device 100 rotates. Subsequently, the snare loading device 100 can once again clamp the snare 170 (as described above) and rotate in the first direction, together with the snare 170. Accordingly, as the snare 170 can be easily rotated through any angle of rotation with one hand, by selectively clamping, rotating, and releasing the snare 170 with the snare loading device 100.

Similarly, the snare 170 can be clamped in the main channel 150 of the main body 110 and advanced into or retracted out of the catheter tube 200 and into and out of the body lumen. Specifically, the wire 172 of the snare 170 can be clamped in the main channel 150, as described above. Subsequently, the snare loading device 100 can be moved toward or away from the catheter tube 200, together with the snare 170. Furthermore, the snare loading device 100 can clamp the snare 170, advance or retract the snare 170, and release the snare 170; such acts can be repeated to advance and/or retract the snare to a desired location.

In some embodiments, the left and right halves of the main body can move away from each other, thereby providing greater access to the main channel located in the main body. Particularly, FIGS. 2A-2D illustrate an exemplary embodiment of a snare loading device 100a that has left and right halves 116a, 118a that are configured to move away from one another. The snare loading device 100a as well as components or elements thereof can be similar to or the same as the snare loading device 100 (FIGS. 1A-1E) and its respective components or elements, except as otherwise described herein.

For example, as illustrated in FIGS. 2A and 2B, the snare loading device 100a can include the main body 110a that has the left and right halves 116a, 118a rotatably coupled together. Particularly, the left and right halves 116a, 118a can be coupled together with a hinge 210a, which can allow the left and right halves 116a, 118a to move away from each other as well as toward each other. In other words, the main body 110a can be in an open configuration, as illustrated in FIG. 2A, when the left and right halves 116a, 118a are rotated away from each other. Conversely, as illustrated in FIG. 2B, the main body 110a can be in a closed configuration, when the left and right halves 116a, 118a are rotated toward each other. In some instance, the hinge 210a can be aligned substantially with a longitudinal axis of the main body 110a.

Moreover, when the main body 110a is in the closed configuration, the left and right halves 116a, 118a can be configured to define a main channel 150a of the main body 110a. For example, the left half 116a can have a portion of the main channel 150a formed therein and the right half 118a can have another, corresponding portion of the main channel 150a. Hence, the opposing portions of the main channel 150a can form the main channel 150a when the left and right halves 116a, 118a are closed together. The main channel 150a can span from a proximal end of the main body 110a to a distal end thereof.

Additionally, the main channel 150a can form an aperture 190a in the distal end of the main body 110a. Consequently, the aperture 190a can reduce the loop of the snare to a desired size and configuration. More specifically, the aperture 190a can reduce the loop to fit into the catheter tube and/or the luer secured thereto.

In additional embodiments, the main body 110a can have a tip 180a at the distal end thereof. For example, the tip 180a can be sized and configured to fit into the catheter tube and/or into the luer attached to the catheter tube. Particularly, the tip 180a can have a tapered configuration, such that the tip 180a has a smaller size at the distal end thereof and a larger size at the proximal in the thereof. Accordingly, the distal end of the tip 180a can fit into the luer. It should be appreciated that the tip 180a and the luer can be coupled, which can define a predetermined and/or fixed position of the snare loading device 100a relative to the catheter tube.

Alternatively, however, the tip 180a can be larger than the lumen of the catheter tube and/or of the luer. As such, the distal end of the tip 180a can abut the catheter tube or the luer secured to the catheter tube, preventing the snare loading device 100a from advancing forward relative to the catheter tube. In any event, the main body 110a and/or the tip 180a can be sized and configured such that the snare loading device 100a can remain stationary relative to the catheter tube at a predetermined location.

Also, as mentioned above, the aperture 190a can reduce the loop, such that the loop can fit inside the lumen of the catheter tube and/or into the luer. Hence, the snare can be pulled in the proximal direction, thereby pulling the loop into the aperture 190a and reducing the loop to be sized and configured to a dimension and shape that is approximately equal to or smaller than the lumen of the catheter tube or the luer.

In some embodiments, the aperture can be tapered and/or can have an inward facing curvature. In particular, the snare loading device can have a tip 180a' and an inward curving aperture 190a', as illustrated in FIG. 2C. Hence, as the loop of the snare enters the aperture 190a', the loop can be compressed thereby. Additionally, however, the loop can outwardly deform the tip 180a'. In some instance, such deformation can reconfigure the aperture 190a' and/or the tip 180a' into a linear, tapered configuration (e.g., tip 180a and aperture 190a (FIG. 2B).

Referring back to FIG. 2B, embodiments described herein can include closure locks 215a', 215" that can secure the left and right halves 116a, 118a together. More specifically, the left and right halves 116a, 118a can include locking sections 216a', 216a" that can correspond with the closure locks 215a', 215a" and lock together, thereby securing the main body 110a in the closed configuration. For instance, the locking sections 216a', 216a" and bottom surfaces of the corresponding closure locks 215a', 215a" can form a friction or interference lock therebetween. The locking sections 216a', 216a" and the corresponding closure locks 215a', 215a" also can have a snap-fit therebetween, which can allow the closure locks 215a', 215a" to snap over the locking sections 216a', 216a".

In additional or alternative embodiments, the snare loading device 100a can include a lock 220a that also can secure the main body 110a in the closed configuration. In other words, the lock 220a can prevent the left half 116a from moving away from the right half 118a. For example, the lock 220a can frictionally secure the left and right halves 116a, 118a together.

In one example, the lock 220a can be secured to the right half 118a. Also, the left half can have a locking section 230a, which can have an interference or friction fit with a portion of the lock 220a, when the main body 110a is in the closed configuration. Specifically, the lock 220a can have a bottom face that can contact the locking section 230a, when the left and right halves 116a, 118a are closed together. Thus, movement of the lock 220a can be impeded by frictional forces between the bottom face thereof and the locking section 230a. Accordingly, the lock 220a can frictionally restrain the left and right halves 116a, 118a from moving away from each other.

Additionally or alternatively, the lock 220a can snap over the locking section 230a. For instance, a leading edge 224a of the lock 220a can contact a portion of the locking section 230a as the left and right halves 116a, 118a move toward each other. Subsequently, the lock 220a can deflect, allowing the lock 220a to pass over the locking portion of the locking section 230a, thereby snapping over the locking section 230a. After the lock 220a snaps over the locking section 230a, in some instances, only a portion of the lock 220a may remain in contact with the locking section 230a (e.g., the leading edge 224a of the lock 220a).

Figure 2D:
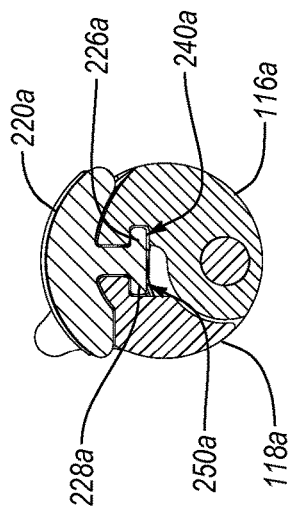
FIG. 2D illustrates a cross-sectional view of the snare loading device of FIG. 2B.

In at least one embodiment, the lock 220a also can move or slide axially in the proximal and/or distal directions along the main body 110a. For example, as illustrated in FIG. 2D, the lock 220a can have a T-shaped lower portion. In other words, the lower portion of the lock 220a can have protruding segments 226a, 228a, which can fit into corresponding slots 240a, 250a in the respective left and/or right halves 116a, 118a. Accordingly, the lock 220a can slide at a predetermined trajectory or path, along the main body within the slots 240a, 250a.

Figure 2E:
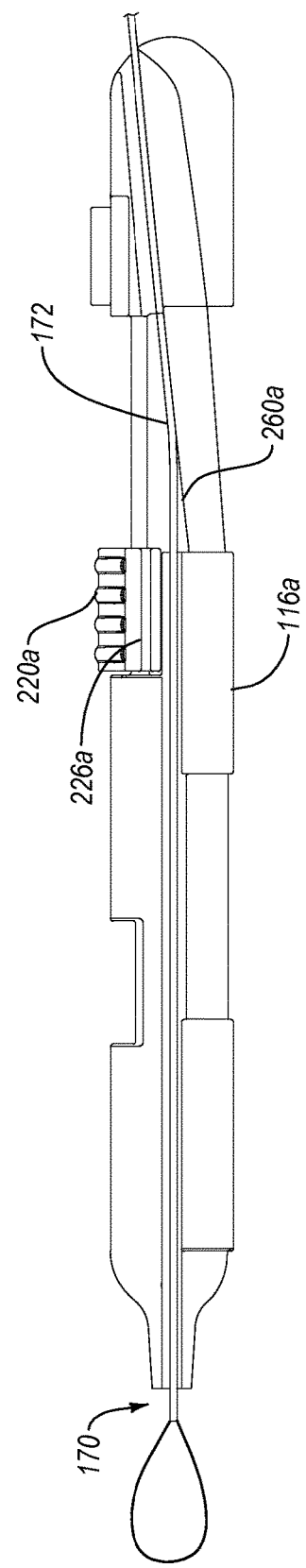
FIG. 2E illustrates a side view of a left half of a main body of the snare loading device of FIG. 2B with a wire of an unclamped snare.
Figure 2F:
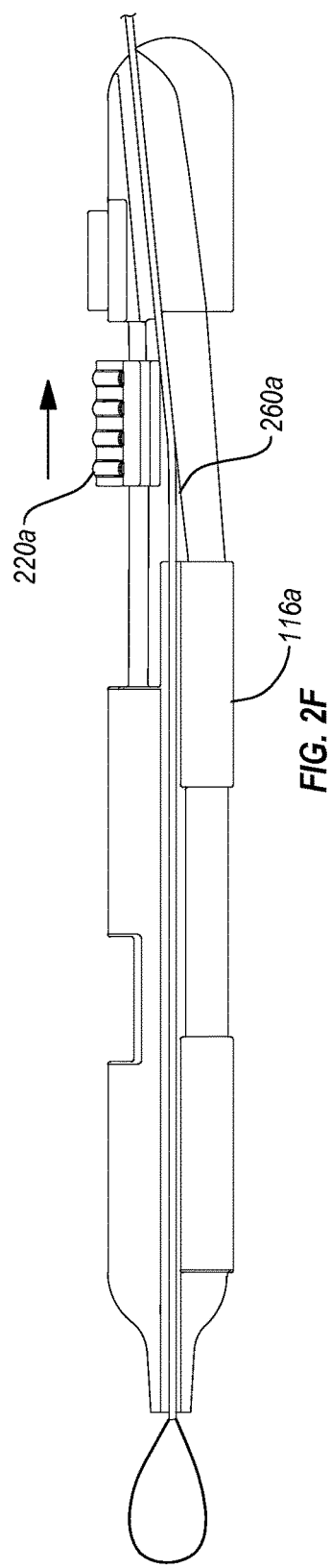
FIG. 2F illustrates a side view of a left half of a main body of the snare loading device of FIG. 2B with the wire of a clamped snare.

Moreover, the lock 220a also can selectively lock or secure the wire of the snare relative to the main body. As such, the snare loading device can transfer radial and axial motion to the snare (as described above). Particularly, as illustrated in FIGS. 2E, 2F, the main channel 150a can have a locking portion 260a, defined between the left and/or right halves 116a, 118a of the main body 110a, which can interface with the lock 220a to secure or couple the wire 172 of the snare 170 to the snare loading device. For instance, the locking portion 260a can be angled toward an upper surface of the main body 110a. In one embodiment, the locking portion 260a can be angled such that a proximal end thereof is closer to the upper surface of the main body 110a than a distal end. Conversely, in other embodiments, the angle of the locking portion 260a can be such that the distal end thereof is closer to the upper surface of the main body 110a than the proximal end.

In any event, the locking portion 260a can be angled toward the lock 220a. At least a portion of the lock 220a can extend into the main channel 150a and/or into the locking portion 260a. As noted above, the wire 172 of the snare 170 can be located in the main channel 150a and into the locking portion 260a thereof. Accordingly, as the lock 220a slides along the locking portion 260a, the distance between the wire 172 and the lock 220a can be reduced, such that the lower portion of the lock 220a can clamp the wire 172 in the locking portion 260a of the main channel 150a. For example, if the proximal end of the locking portion 260a is closer to the upper surface of the main body 110a than the distal end of the locking portion 260a, as the lock 220a slides in the proximal direction, the lower portion of the lock 220a can clamp the wire 172 in the locking portion 260a. Conversely, as the lock 220a slides in the opposite direction (i.e., distally), the lock 220a can unclamp the wire 172, such that the snare loading device is free to move relative to the snare 170.

When the lock 220a clamps the wire 172 in the locking portion 260a, the snare 170 is coupled or secured to the snare loading device. Thus, the snare loading device can transfer axial and radial motion to the snare 170, as described above. Moreover, the snare loading device can selectively secure and release the snare 170, as may be desired. In at least one example, the lock 220a can be operated with a finger or a thumb. Consequently, the snare loading device can secure and release the snare 170 in response to a single quick movement of the lock 220a, initiated by a user's finger.

In one or more embodiments, movement of the lock 220a can be frictionally impeded by the locking section 230a (FIG. 2C). Accordingly, the friction between the lock 220a and the locking section 230a can prevent inadvertent release or decoupling of the snare 170 from snare loading device. For instance, the frictional contact between the locking section 230a and the lock 220a can ensure that the lock 220a remains in the locked position, securing snare 170, as the snare loading device 100a is manipulated to transmit motion to the snare 170.

Figure 2G:
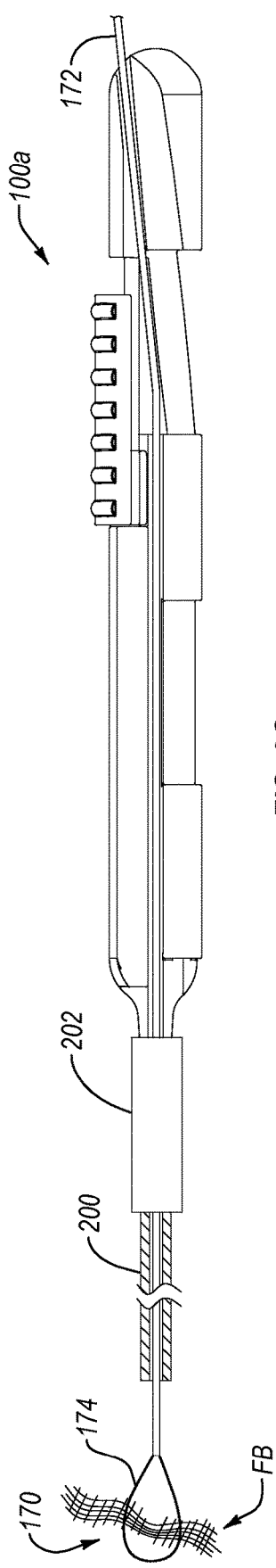
FIG. 2G illustrates a partial side view of the snare loading device of FIG. 2B coupled to a catheter tube in accordance with one embodiment of the present invention.
Figure 2H:
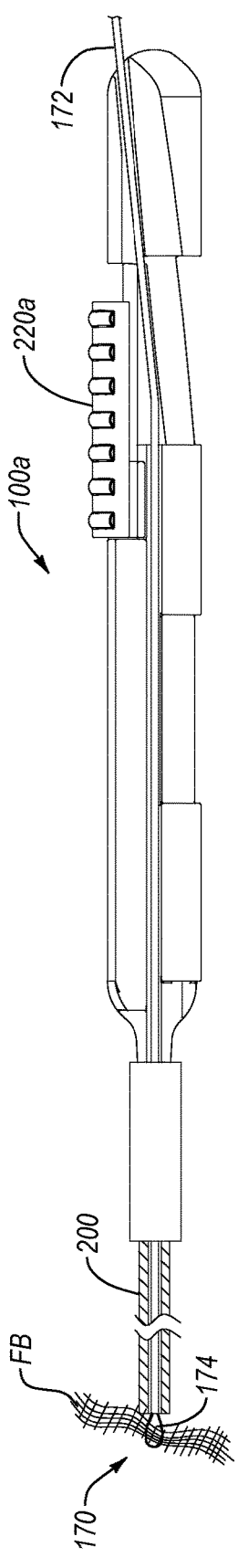
FIG. 2H illustrates a partial side view of the snare loading device of FIG. 2B coupled to a catheter tube and securing a foreign body in accordance with one embodiment of the present invention.
Figure 2I:
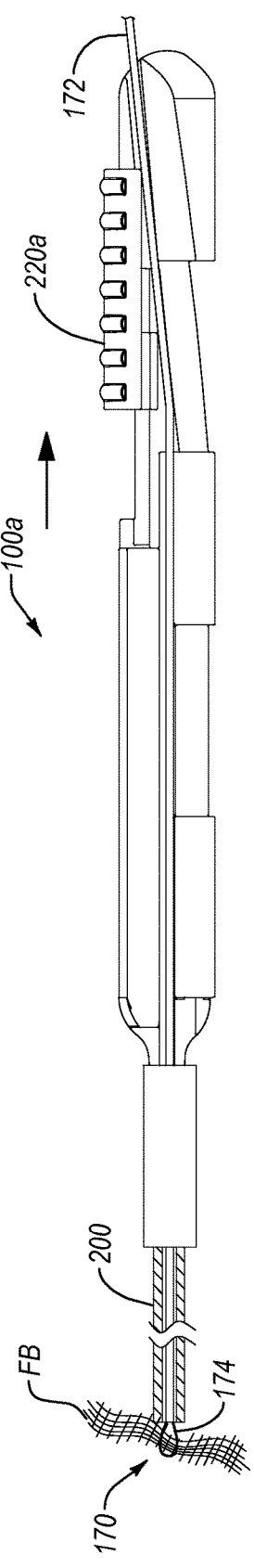
FIG. 2I illustrates a partial side view of the snare loading device of FIG. 2B coupled to a catheter tube and in a locked configuration, the snare loading device securing a foreign body in accordance with one embodiment of the present invention.

Furthermore, the snare loading device 100a (as well as any other embodiment of the snare loading device, as described herein) can be used to capture and secure a foreign object relative to the catheter tube 200, as illustrated in FIGS. 2G-2I. Subsequently, the foreign object can be removed together with the catheter tube 200 and the snare loading device 100a. More specifically, the snare 170 can be guided by the snare loading device 100a through the luer 202, through the catheter tube 200, and into a body lumen or cavity. As the loop 174 of the snare 170 exits the catheter tube 200, the snare loop 174 can expand into the expanded configuration (FIG. 2G).

Thereafter, the snare 170 can be navigated to capture a foreign body FB. For example, various techniques can be used to manipulate the snare 170 into position and to capture the foreign body FB, such as advancing, retracting, rotating, etc., the snare 170. Once the loop 174 of the snare 170 is positioned about the foreign body FB, the snare 170 can be retracted, such that the loop 174 is pulled into the catheter tube 200 and at least partially collapsed thereby around the foreign body (FIG. 2H). It should be appreciated that the wire 172 of the snare 170 can be movable through the snare loading device 100a. In other words, the lock 220a can be disengaged from the wire 172, to allow the snare 170 to be pulled proximally relative to the catheter tube 200.

Once the foreign body FB is secured within the loop 174 and/or against the catheter tube 200, the lock 220a can be operated to engage and lock the wire 172, thereby securing the snare 170 relative to the snare loading device 100a. Accordingly, the foreign body FB can be secured and locked within the loop 174 of the snare 170 and/or against catheter tube 200. Hence, the foreign body FB can be removed from the patient by removing the snare loading device 100a together with the catheter tube 200 and together with the foreign body FB secured thereto.

Figure 3C:
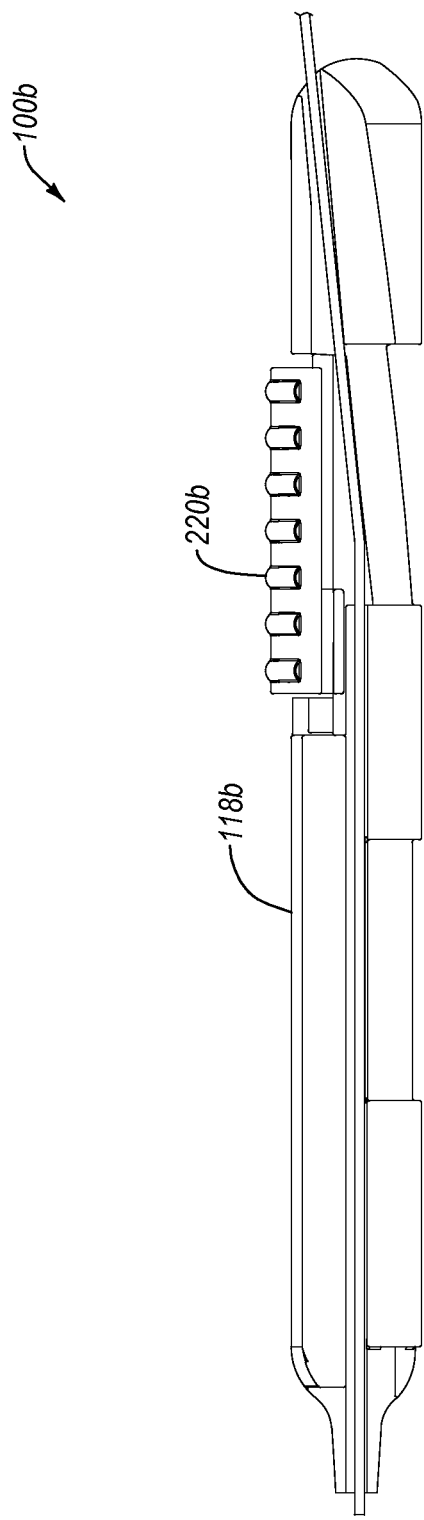
FIG. 3C illustrates a side view of a right half of a main body of the snare loading device of FIG. 3B in an unlocked configuration and with an unclamped snare.

Additionally or alternatively, as illustrated in FIGS. 3A-3E, the snare loading device can have a lock that positively locks and secures the left and right halves of the main body together. Particularly, as illustrated in FIG. 3A, a snare loading device 100b that can include a main body 110b that has left and right halves 116b, 118b, which can be secured together by a lock 220b. The snare loading device 100b and any component or element thereof can be similar to or the same as any one of the snare loading device 100, 100a (FIGS. 1A-2E) and their corresponding components and elements, except as otherwise described herein.

In one embodiment, the main body 110b can have proximal locking tabs 270b, 280b and distal locking tabs 270b', 280b' that can accept the lock 220b, which can secure the main body 110b in the closed configuration (illustrated in FIG. 3B). In other words, the left half 116b can have the proximal and distal locking tabs 270b, 270b', and the right half 118b can have the proximal and distal locking tabs 280b, 280b', which can be located opposite to the respective proximal and distal tab 270b, 270b'. For instance, the proximal locking tabs 270b, 280b can be located near the respective proximal ends of the left and right halves 116b, 118b. By contrast, the distal locking tabs 270b', 280b' can be located distally from the proximal locking tabs 270b, 280b, along the length of the main body 110b, as illustrated in FIG. 3B. In one example, when the main body 110b is in the closed configuration (i.e., the left and right halves 116b, 118b are together), the lock 220b can slide over the proximal locking tabs 270b, 280b, thereby securing the left and right halves 116b, 118b together. It should be appreciated that the lock 220b also can slide of the distal locking tabs 270b', 280b' to lock the left and right halves 116b, 118b together.

Figure 3D:
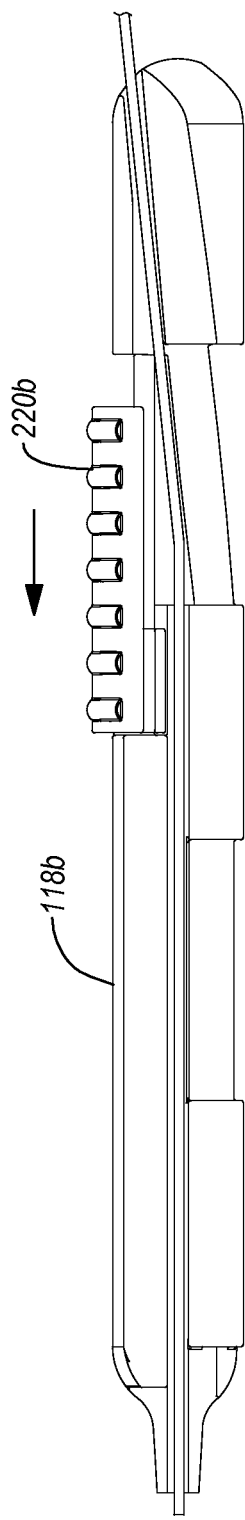
FIG. 3D illustrates a side view of a right half of a main body of the snare loading device of FIG. 3B in a locked configuration and with an unclamped snare.
Figure 3E:
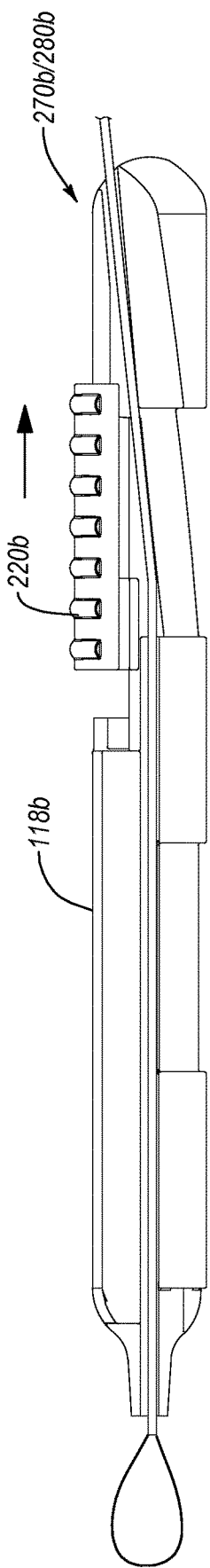
FIG. 3E illustrates a side view of a right half of a main body of the snare loading device of FIG. 3B in another locked configuration and with a clamped snare.

FIGS. 3C-3F illustrate exemplary sequences of movements of the lock 220b, which can lock the main body 110b in the closed configuration. Particularly, the lock 220b can slide in the distal direction over the distal locking tabs (FIGS. 3C, 3D). As illustrated in FIG. 3D, when a front edge of the lock 220b passes over the distal locking tabs 270b', 280b', the lock 220b can secure the left and right halves 116b, 118b together. Alternatively, as illustrated in FIG. 3E, the lock 220b can slide in the proximal direction, over the proximal locking tabs 270b, 280b, thereby holding the proximal locking tabs 270b, 280b together and securing the main body in the closed configuration.

Figure 3F:
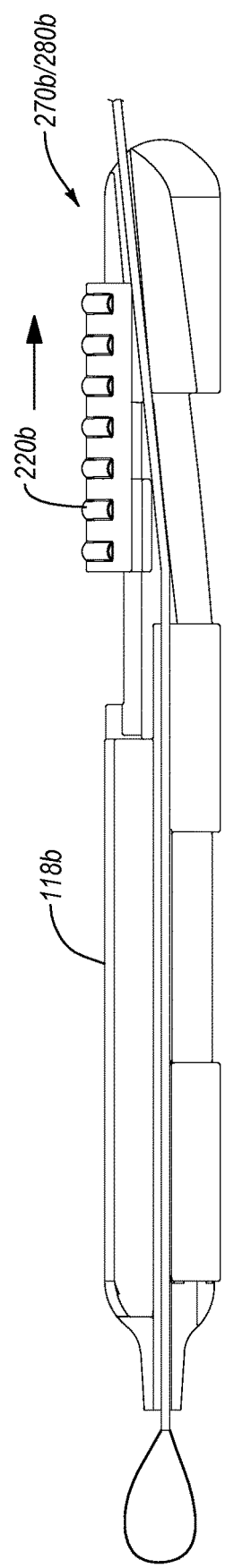
FIG. 3F illustrates a side view of a right half of a main body of the snare loading device of FIG. 3B in another locked configuration and with a clamped snare.

Similar to the snare loading device 100a (FIGS. 2A-2F), as illustrated in FIG. 3F, the lock 220b also can secure the wire 172 of the snare 170 in a main channel. The main channel 150b of the snare loading device can have a locking portion 260b, which can allow the lock 220b to secure the wire 172 to the main body 110b. In some embodiments, the locking portion 260b can cooperate with the lock 220b in a manner that allows the lock 220b to secure the left and right halves 116b, 118b together, while maintaining the wire 172 uncoupled within the main channel 150, as illustrated in FIGS. 3D-3E.

Specifically, the lock 220b can have a locking protrusion 290b which can secure the wire 172 to the locking portion 260b of the main channel 150b. The lock 220b also can have a T-shaped configuration therein, which can allow the lock 220b to slide over the proximal locking tabs 270b, 280b and secure the left and right halves 116b, 118b together, as described above. Particularly, as the leading edge of the lock 220b enters the proximal locking tabs 270b, 280b, the T-shape of the lock 220b can engage the proximal locking tabs 270b, 280b and lock the left and right halves 116b, 118b together.

In at least one embodiment, as noted above, the locking portion 260b can be substantially the same as locking portion 260a (FIGS. 2E-2F). Accordingly, as illustrated in FIG. 3E, the lock 220b can continue moving in the proximal direction over the tabs 270b, 280b until the lock 220b contacts and clamps the wire 172 within the locking portion 260b. Thus, the lock 220b can be operated to lock the left and right halves 116b, 118b together independently of locking and/or securing the snare 170 within the main channel 150b.

In other words, for example, the main body 110b can be closed and secured in the closed configuration by the lock 220b to allow the loop 174 of the snare 170 to be pulled into the main channel 150b to reduce the loop 174 to a desired size and configuration (e.g., as described above). Subsequently, the snare loading device 100b can be coupled to the snare 170 to allow the snare loading device 100b to selectively transmit axial and/or radial motion to the snare 170. Specifically, the lock 220b can be operated to couple the snare 170 to the main body 110b and to release the snare 170 therefrom, to control the movement of the snare 170 within the lumen of the catheter tube and/or within the body lumen.

As described above, the left and right halves of the main body can move away from each other by rotating about a hinge. Specifically, the hinge can be oriented parallel to a longitudinal axis of the main body. It should be appreciated, however, that this disclosure is not so limited. In some embodiments, the left and right halves of the main body move away from each other by rotating about a hinge oriented with respect to a different axis.

Figure 4A:
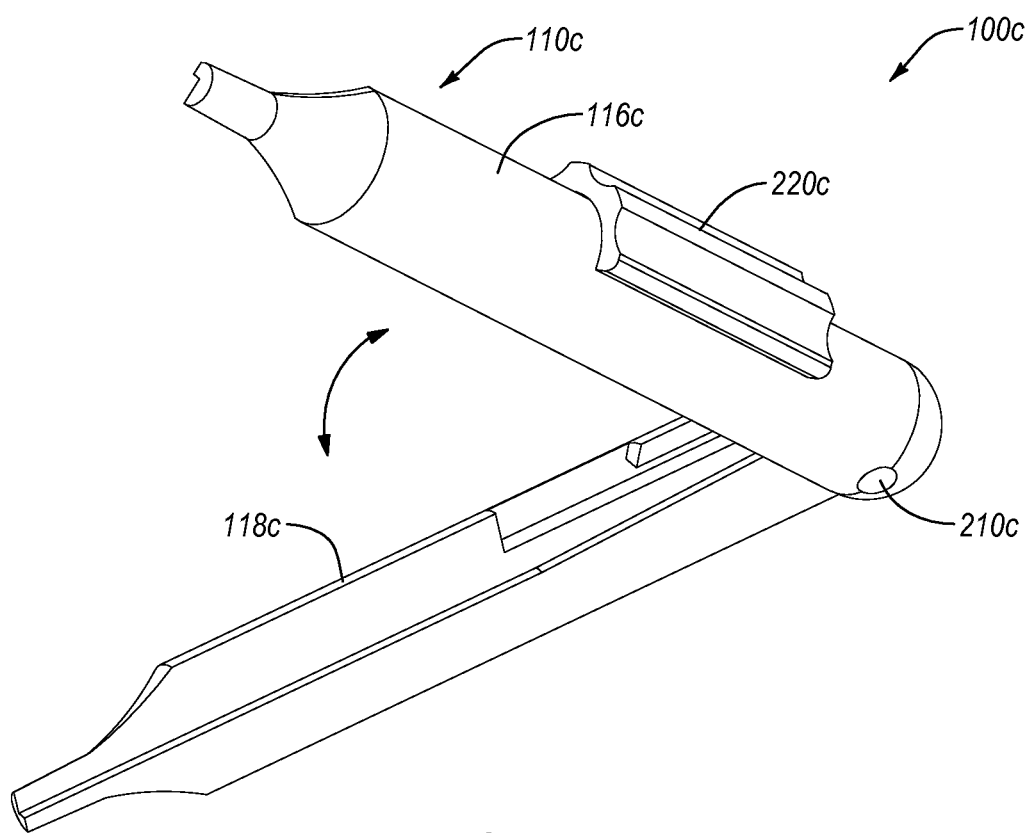
FIG. 4A illustrates a perspective view of a snare loading device in an open configuration in accordance with still one other embodiment of the present invention.

For example, as illustrated in FIG. 4A, a snare loading device 100c can include a main body 110c that has left and right halves 116c, 118c rotatably coupled together by a hinge 210c. Except as otherwise described herein, the snare loading device 100c and any components or elements thereof can be similar to or the same as any one of the snare loading devices 100, 100a, 100b (FIGS. 1A-3E) and their respective elements and components. In some embodiments, the hinge 210c can be oriented substantially perpendicularly relative to the longitudinal axis of the main body 110c. Hence, the left and right halves 116c, 118c can move away from each other to the open configuration illustrated and FIG. 4A.

Figure 4B:
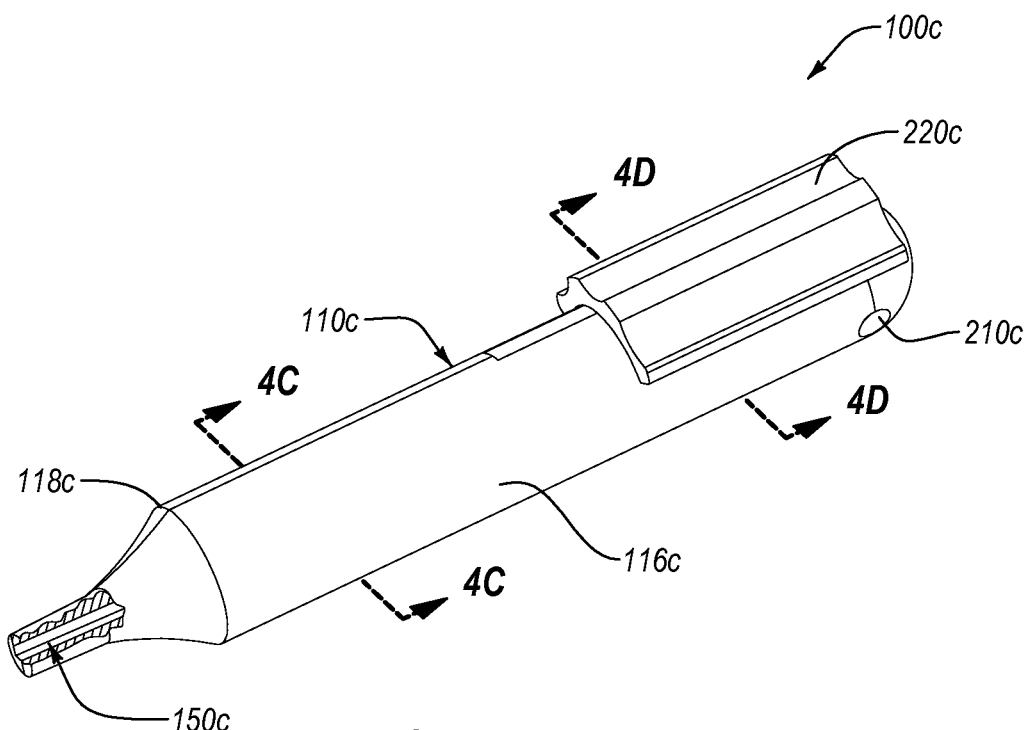
FIG. 4B illustrates a perspective view of the snare loading device of FIG. 4A in a closed configuration.

Likewise, the left and right halves 116c, 118c can be rotated and brought close together, to reconfigure the main body 110c into closed configuration, as illustrated in FIG. 4B. The snare loading device 100c also can include a lock 220c that can lock the left and right halves 116c, 118c together, as further described below. Accordingly, the left and right halves 116c, 118c can move away from each other to facilitate placement of the snare within a main channel 150c in the main body 110c.

Figure 4C:
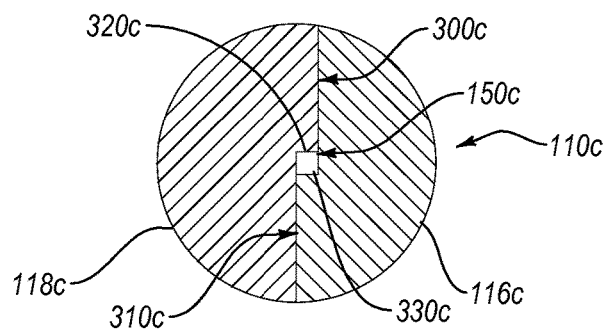
FIG. 4C illustrates a cross-sectional view of the snare loading device of FIG. 4B.

As illustrated in FIG. 4C, in one embodiment, the main body 110c can include a main channel 150c that has a rectangular or square cross-sectional shape. For instance, the main channel 150c can be formed by portion of the opposing left and right halves 116c, 118c. Particularly, the main channel 150c can be formed by opposing inside faces 300c, 310c of the left and right halves 116, 118c and by corresponding ledges 320c, 330c thereof. In some instance, the inside faces 300c, 310c can be substantially flat. Additionally, the ledges 320c, 330c can define respective, opposing upper and lower sidewalls of the main channel 150c.

The cross-section of the main channel 150c can be sized to accept at least a portion of the snare therein. For example, the main channel 150c can be sized such that the wire of the snare can move freely or loosely therein. Alternatively, however, the wire of the snare can have a snug fit within the main channel 150c.

Figure 4D:
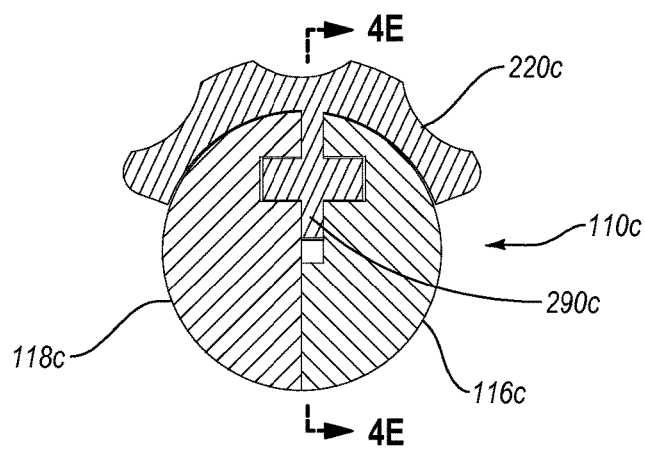
FIG. 4D illustrates another cross-sectional view of the snare loading device of FIG. 4B.

As described above, the lock 220c can lock the main body 110c in the closed configuration. More specifically, as illustrated in FIG. 4D, the lock 220c can have a T-shaped lower portion, which can fit into opposing slots in the left and right halves 116c, 118c that, when the main body 110c is in the closed configuration, together form a T-slot. As the T-shaped lower portion of the lock 220c fits into the opposing slots, the lock 220c can prevent the left and right halves 116c, 118c from rotating about the hinge 210c (FIGS. 4A, 4B).

As shown in FIGS. 4A-4B, the lock 220c can slide in the proximal and/or distal directions, in alignment with the longitudinal axis of the main body 110c. Accordingly, the T-shaped portion of the lock 220c can slide into the slots located in the left and right halves 116c, 118c to lock the main body 110c in the closed configuration (FIG. 4B). Conversely, the lock 220c can slide out of the opposing slots in the left and right halves 116c, 118c, thereby allowing the left and right halves 116c, 118c, to rotate away from each other about the hinge 210c (FIG. 4A).

Figure 4E:
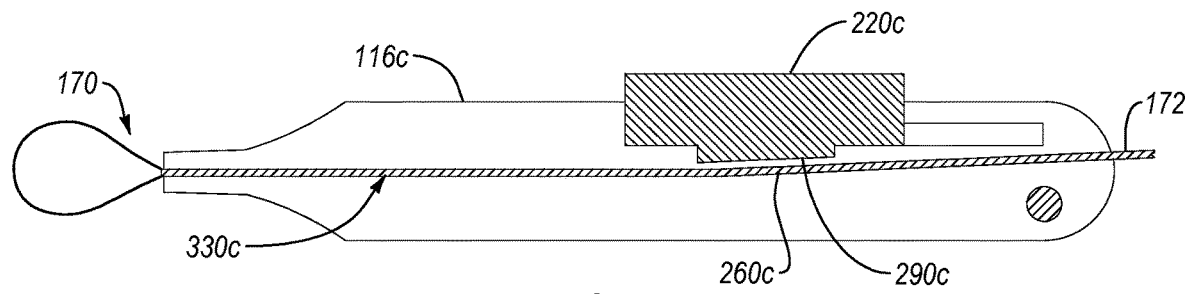
FIG. 4E illustrates a cross-sectional view of the snare loading device of FIG. 4D with an unclamped snare.
Figure 4F:
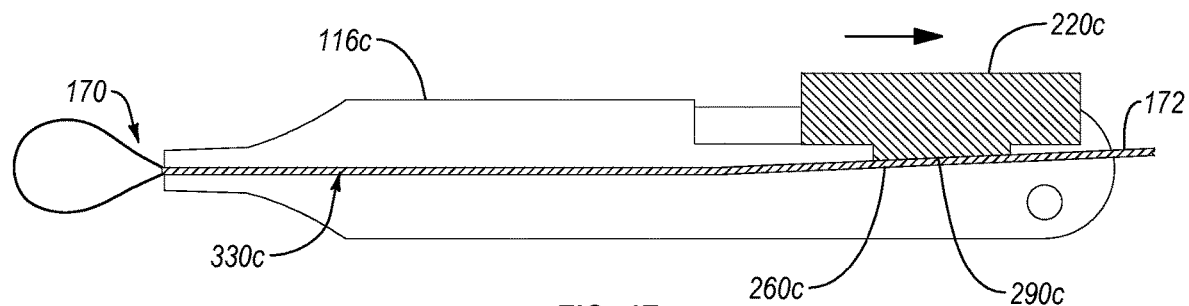
FIG. 4F illustrates a cross-section view of the snare loading device of FIG. 4B with clamped snare.

Similar to the lock 220a, 220b (FIGS. 2A-3E), the lock 220c can secure the snare in the main body 110c. For example, as illustrated in FIGS. 4E-4F (and described above), the lock 220c can slide in the proximal and/or distal directions, in alignment with the longitudinal axis of the main body. Moreover, the channel in the main body can have an angled locking portion 260c (similar to main channel 150a (FIGS. 2A-2E).

In one embodiment, the ledge 330c, which defines the bottom potion of the channel, can be angled and can form the locking portion 260c of the main channel. The angle can be such that the ledge 330c is closer to the upper surface of the main body at a proximal end of the ledge 330c than at a distal end thereof. Alternatively, a distal end of the ledge 330c can be located closer to the upper surface of the main body. Moreover, only a portion of the ledge 330c (e.g., a locking portion 260c) can be angled. Hence, the angle of the ledge 330c and/or the angle of the locking portion 260c can be configured in any number of ways, which can vary from one embodiment to the other.

In any event, the locking portion 260c can be configured such that a locking protrusion 290c of the lock 220c can clamp the wire 172 of the snare 170 in the main channel 150c. Particularly, as illustrated in FIG. 4F, in one embodiment, the lock 220c can move in the proximal direction, thereby clamping the wire 172 of the snare 170 between the locking protrusion 290c and the locking portion 260c of the ledge 330c. Equally, the lock 220c can move in the distal direction to release or unclamp the snare 170. In any case, the lock 220c can be operated to selectively secure and release the snare 170 from the snare loading device, which can allow selective transmittal of motion from the snare loading device to the snare.

Figure 5A:
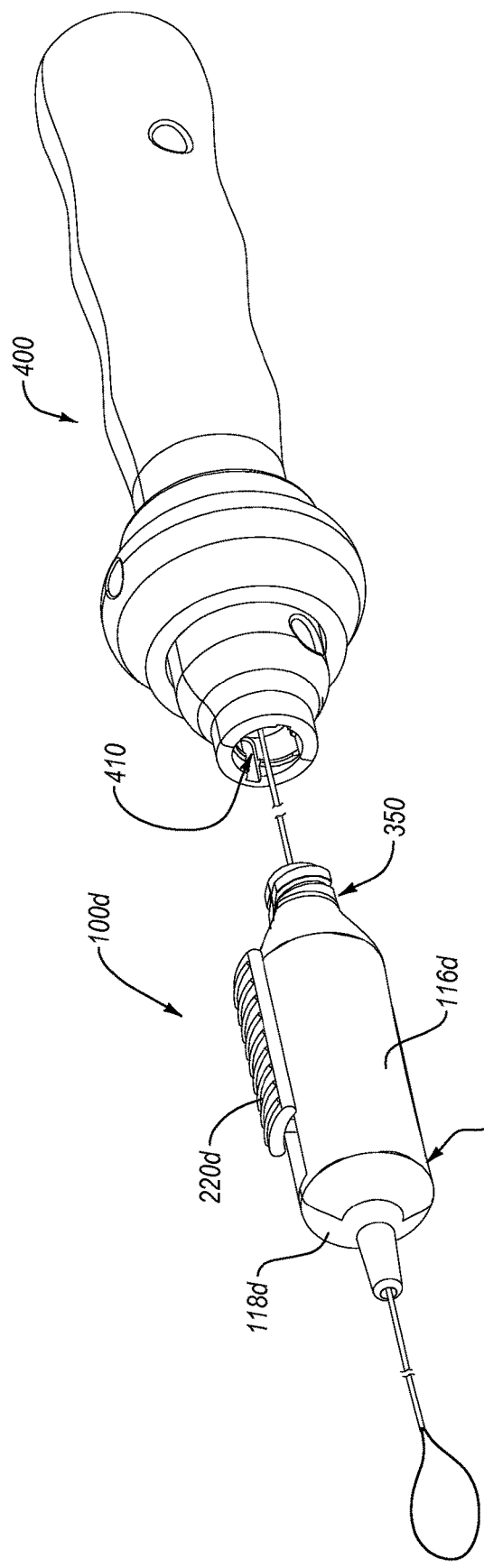
FIG. 5A illustrates a perspective view of a snare loading device and a handle in accordance with one embodiment of the present invention.
Figure 5B:
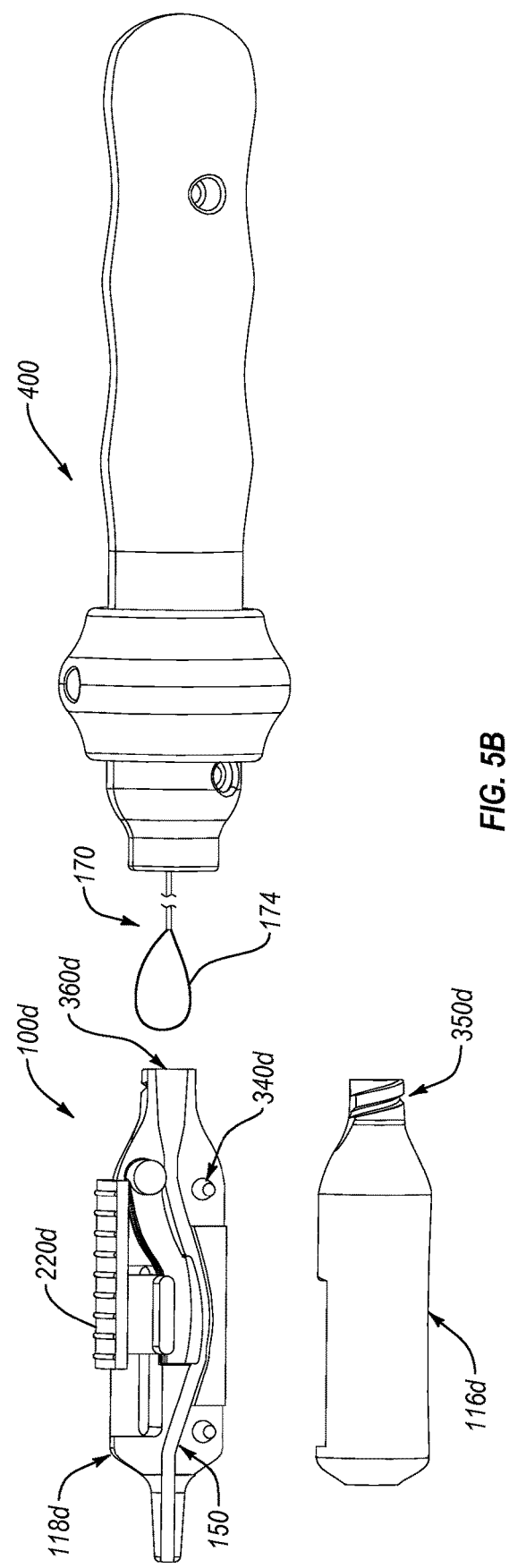
FIG. 5B illustrates an exploded perspective view of the snare loading device of FIG. 5A.

In some embodiments, the snare loading device can incorporate a curvilinear main channel. For example, as illustrated in FIGS. 5A-5B, a snare loading device 100d can incorporate a curvilinear main channel 150d located between and/or defined by left half 116d and right half 118d, which also can define a main body 110d. Except as otherwise described herein, the snare loading device 100d and any components or elements thereof can be similar to or the same as any one of the snare loading devices 100, 100a, 100b, 100c (FIGS. 1A-4F) and their respective elements and components. In one or more embodiments, such curvilinear main channel 150d can reduce snagging or binding of the wire 172 of the snare 170 as the wire 172 is pulled through the main channel 150d. Additionally, the curvilinear main channel 150d also can improve locking of the wire 172 therein and relative to the snare loading device 100d.

In one exemplary embodiment, the left half 116d and the right half 118d of the snare loading device 100d can detachably couple together. For example, the right half 118d can have a single or multiple dowel pins or protrusions 340d, which can fit into corresponding recesses in the left half 116d. Hence, the portion of the curvilinear main channel 150d located in the left half 116d can be aligned with the corresponding portion of the curvilinear main channel 150d located in the right half 118d, when the two halves are connected together (as shown in FIG. 5A).

Additionally, the snare loading device 100d can have a thread 350d (e.g., an external thread) that can correspond with a thread on a handle 400, which can couple to the snare loading device 100d. For instance, the handle 400 can include internal thread 410 that mesh and couple with the thread 350d of the snare loading device 100d. It should be appreciated that the right half 118d and left half 116d can have any desirable configuration, dividing the snare loading device 100d into two portions. Specifically, the right half 118d and the left half 116d need not be the same or mirror images of each other (e.g., the snare loading device 100d need not be split about a centerline thereof to form the right half 118d and left half 116d). Hence, portions of the thread 350d can be located on the respective left half 116d and right half 118d in a manner that the left half 116d and right half 118d form the thread 350d when coupled together. In addition, the snare loading device 100d need not be split into halves 118d and 116d, but rather may be split into multiple portions (i.e. three or more).

Furthermore, particular coupling mechanism between the snare loading device 100d and the handle 400 can vary from one implementation to another. For instance, the snare loading device 100d and the handle 400 can be press-fit together. Alternatively, the snare loading device 100d and the handle 400 can couple via detents or otherwise snap-in together. Also, in some embodiments, the snare loading device 100d may have not coupling mechanism with the handle 400.

In one embodiment, the protrusions 340d can be press fit into the corresponding recesses, thereby coupling the left half 116d to the right half 118d. Additionally or alternatively, the thread 350d, when coupled within the internal thread 410, can couple the left half 116d and right half 118d together. Accordingly, the thread 350d and internal thread 410 can couple the snare loading device 100d to the handle 400 and can hold together the left half 116d and right half 118d of the snare loading device 100d.

The main body 110d also can have a collapsing taper 360d, which can reduce the size of the loop 174 of the snare 170, as the loop 174 is forced into the snare loading device 100d. The collapsing taper 360d can connect to or merge with the main channel 150d. Thus, the loop 174 can be forced into the collapsing taper 360d, which can compress the loop 174 in a manner so that the snare 170 (i.e., the loop 174 and the wire of the snare 170) can travel through the curvilinear main channel 150d. Moreover, as further described below, the snare can exit the curvilinear main channel 150d and can enter the catheter tube, to be guided to a desired location or position in the body.

Figure 5C:
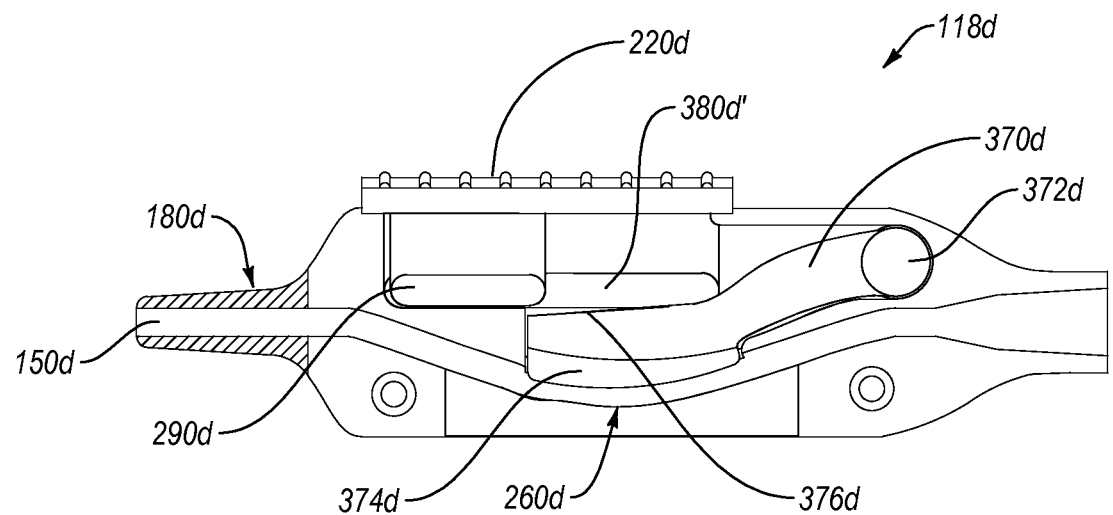
FIG. 5C illustrates a side view of a left half of a main body of the snare loading device of FIG. 5A.
Figure 5D:
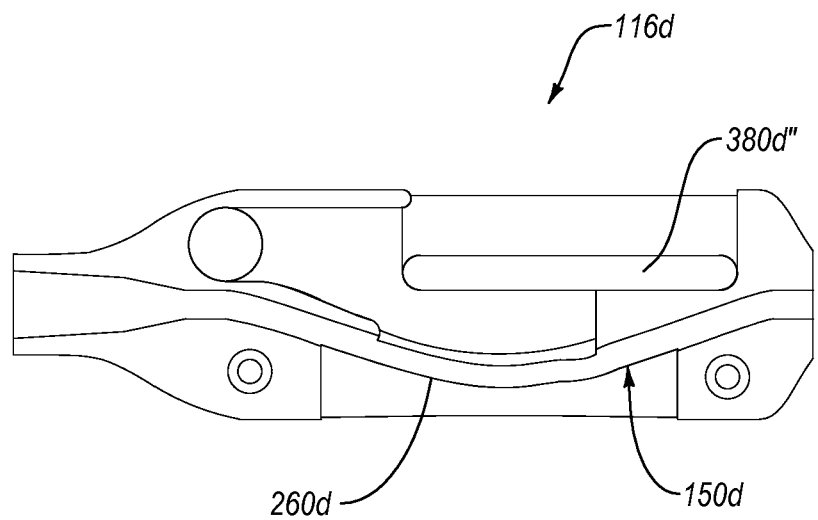
FIG. 5D illustrates a side view of a left half of a main body of the snare loading device of FIG. 5A.

In at least one embodiment, the snare loading device 100d also can incorporate a lock 220d that can secure or immobilize the snare 170 relative to the snare loading device 100d. Particularly, FIGS. 5C-5D illustrate the right half 118d and left half 116d, respectively, which exemplify one embodiment of the snare loading device that incorporates the lock 220d. As illustrated in FIG. 5C, the lock 220d can move in a lateral direction (i.e., toward a proximal or distal ends of the snare loading device 100d) to actuate a cam 370d, which can clamp or crimp the wire of the snare in the main channel 150d. For instance, the curvilinear main channel 150d can include a locking portion 260d, which can interface with the cam 370d, thereby clamping the wire of the snare therebetween. As can be seen in FIGS. 5C and 5D, the main channel 150d, as well as the locking portion 260d thereof can be formed by the right half 118d and left half 116d.

Also, the locking portion 260d can curve away from the lateral center axis of the snare loading device. For example, the locking portion 260d can curve downward and away from the lock 220d and/or from the cam 370d. Accordingly, the cam 370d can move downward or into the curve of the locking portion 260d to lock or clamp the wire of the snare therein.

As noted above, the curve of the curvilinear main channel 150d can facilitate insertion of the snare into the snare loading device, while avoiding kinking of the snare as well as snagging or binding of the snare on the lock 220d and/or cam 370d. In one or more embodiments, the curve of the curvilinear main channel 150d may be at least in part formed by the curve of the locking portion 260d thereof. Furthermore, as the snare passes through the locking portion 260d of the curvilinear main channel 150d, the snare can move downward and away from the cam 370d (when the cam 370d is in a disengaged position). As such, collision or contact of the snare with the cam 370d can be avoided or minimized. Minimizing or avoiding contact of the snare with the cam 370d can reduce or eliminate snagging or binding of the snare on the cam 370d.

In some embodiments, the cam 370d can be rotatably coupled to the main body of the snare loading device. Particularly, the cam 370d can be rotatable about a cam axis 372d. Hence, the cam 370d can be rotated toward and away from the locking portion 260d of the curvilinear main channel 150d.

The cam 370d also can have a locking bottom portion 374d that can contact and clamp the wire of the snare against and within the locking portion 260d of the curvilinear main channel 150d, when the cam 370d rotates downward, toward the locking portion 260d. For example, the locking bottom portion 374d can have a curvilinear shape, which can approximate the curvilinear shape of the locking portion 260d of the main channel 150d.

The cam 370d also can include an angled section 376d, which can interface with the lock 220d. For example, as the lock 220d moves in the proximal direction, a lower portion 290d of the lock 220d can engage the angled section 376d of the cam 370d. Moreover, as the lower portion 290d moves proximally relative to the cam 370d, the lower portion 290d can push against the angled section 376d and can push the cam 370d downward, in a manner that the cam 370d rotates about the cam axis 372d and clamps the wire of the snare against the locking portion 260d of the main channel 150d.

It should be appreciated that particular location and orientation of the cam 370d and the cam axis 372d can vary from one embodiment to another. Accordingly, in some embodiments, the cam 370d can be rotated upward (toward the lock 220d), thereby engaging and locking the wire of the snare in the locking portion 260d of the main channel 150d. As such, the locking portion 260d also can have a corresponding orientation (i.e., curving upward, or toward the lock 220d), such that the cam 370d can rotate toward the locking portion 260d and clamp the wire of the snare relative thereto.

As noted above, the lock 220d can slide in the proximal and distal directions along the main body of the snare loading device. In at least one embodiment, the main body can include a channel or a groove that can guide the lock 220d. For example, the right half 118d and the left half 116d can include corresponding grooves 380d', 380d'', which can receive the lower portion 290d of the lock 220d and can guide the lock 220d along the main body (e.g., the grooves 380d', 380d'' can guide the lock 220d on a substantially linear trajectory).

The main body of the snare loading device also can include a tip 180d. As mentioned above, the tip 180d can be configured to couple to a luer, which can facilitate advancing the snare through the snare loading device and into the catheter tube that incorporates a luer. In one or more embodiments, the entire tip 180d can be located on the right half 118d (FIG. 5C). Accordingly, the left half 116d (FIG. 5D) can form no portion of the tip 180d. Hence, the tip 180d can be substantially monolithic, which can improve rigidity and reduce snagging or binding of the snare in the main channel 150d as the snare passes through the tip 180d of the snare loading device (as compared with a tip that is formed from two distinct portions). Nevertheless, in other embodiments, the tip 180d can be formed in part by the right half 118d and in part by the left half 116d.

Capability of inserting the snare from a back or proximal side of the snare loading device, can allow the snare loading device to be used with snares that incorporate various tools or devices on a back or proximal end thereof (e.g., snares that include a handle, such as the handle 400 (FIGS. 5A-5B). In other words, because the snare's distal end (or the loop thereof) is inserted first into the snare loading device, such a snare can include various equipment or tools on the proximal ends thereof, which will not interfere with the insertion. Particularly, as illustrated in FIGS. 5E-5I, the snare loading device 100d can be used to advance the snare 170 to a desired location, secure a foreign object FB, and remove the foreign object FB from the patient's body.

Figure 5E:
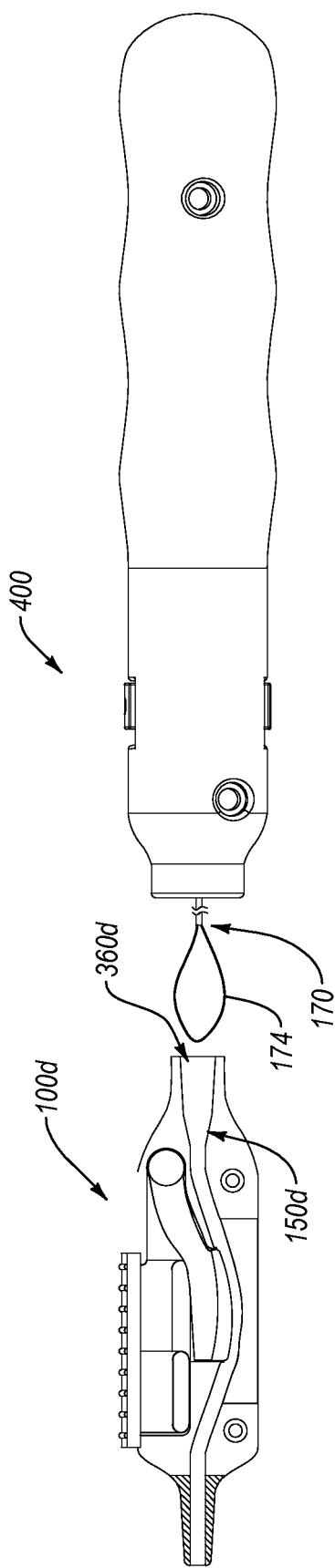
FIG. 5E illustrates an act of using a snare loading device in accordance with one embodiment of the present invention.
Figure 5F:
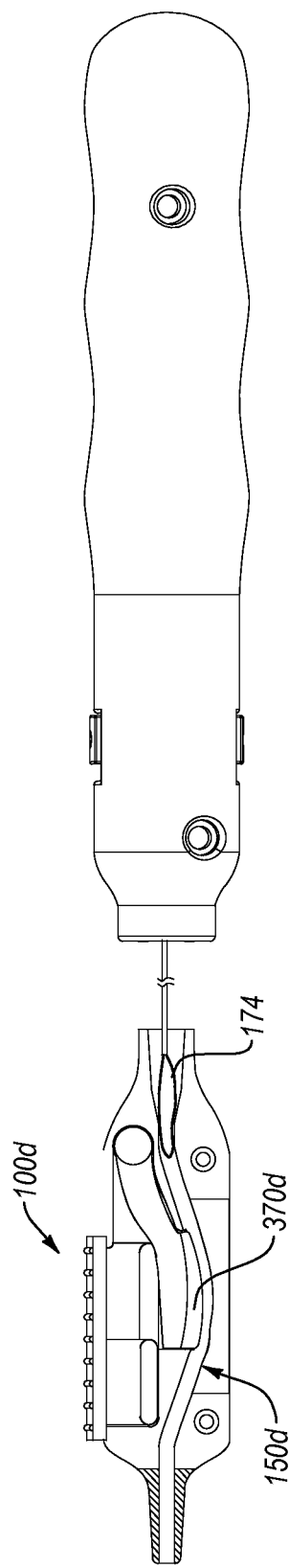
FIG. 5F illustrates another act of using a snare loading device in accordance with one embodiment of the present invention.

For instance, the loop 174 of the snare can be inserted into the collapsing taper 360d of the snare loading device 100d (FIGS. 5E-5F). As the loop 174 of the snare 170 is pushed into the collapsing taper 360d, the collapsing taper 360d can gradually collapse the loop 174, as the loop 174 travels through the collapsing taper 360d and into the main channel 150d. Hence, as the loop 174 enters the main channel 150d, the loop 174 can be sufficiently collapsed to fit therein (FIG. 5F). Thereafter, the snare 170 and the loop 174 can be advanced forward, through and out of the snare loading device 100d.

The lock 220d can be positioned in the unlocked location. For instance, the lock 220d can be advanced to a farthest distal position. Thus, the cam 370d can be substantially free to rotate upward or away from the main channel 150d. In the event the cam 370d is positioned in a downward location, as the loop 174 of the snare moves through the main channel 150d and contacts the cam 370d, the loop 174 can push the cam 370 upward, in a manner that creates sufficient space for the loop 174 to pass along the main channel 150d. Also, the locking bottom portion of the cam 370d can have rounded or curvilinear contours, which can facilitate the loop 174 engaging and moving the cam 370d upward without snagging or binding thereon. In other words, the cam 370d can be free to move upward in response to pressure applied thereto by the snare 170, when the lock 220d is in the unlocked position.

Figure 5G:
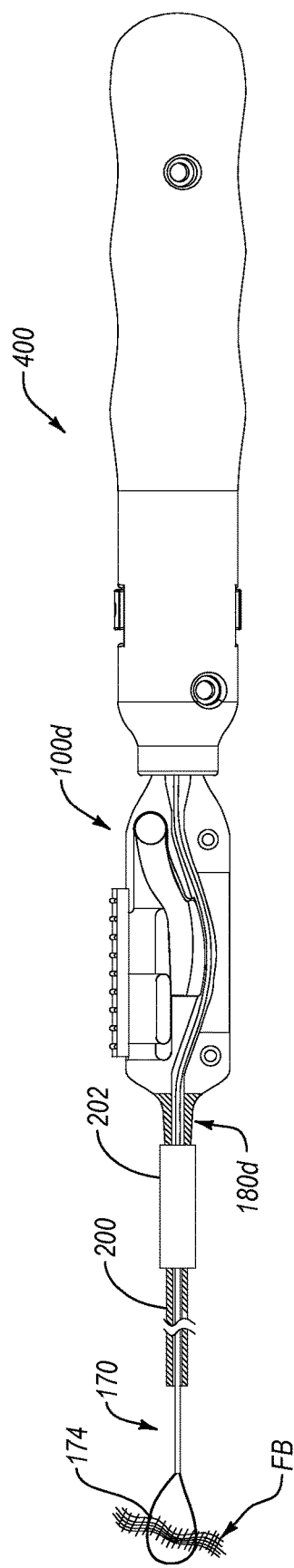
FIG. 5G illustrates yet one other act of using a snare loading device in accordance with one embodiment of the present invention.

As described above, the tip 180d of the snare loading device 100d can be coupled to the luer 202 of the catheter tube 200 (FIG. 5G). Consequently, the snare 170 can be advanced through the snare loading device 100d, through the luer 202, and into the catheter tube 200. Furthermore, the snare can exit the catheter tube 200, allowing the loop 174 of the snare 170 to expand into the expanded configuration.

Also, as the snare 170 is fed through the snare loading device 100*d*, the handle 400, which can be coupled to the snare 170, can reach the snare loading device 100*d*. Hence, in at least one embodiment, the snare loading device 100*d* can couple to the handle 400, in a manner descried above. Thus, the handle 400 and the snare loading device 100*d* can form a single body that can be manipulated and/or controlled by a user.

Figure 5H:
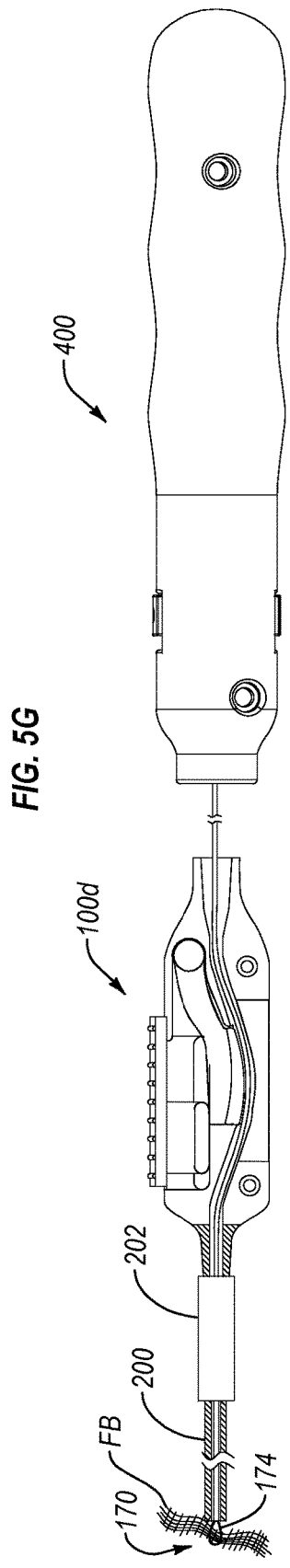
FIG. 5H illustrates still another act of using a snare loading device in accordance with one embodiment of the present invention.
Figure 5I:
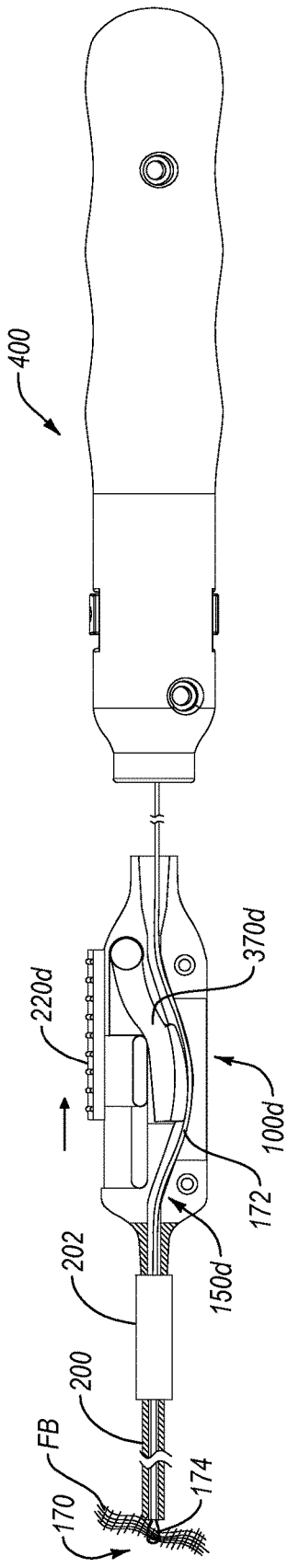
FIG. 5I illustrates an additional act of using a snare loading device in accordance with one embodiment of the present invention.

Moreover, as described above, the snare 170 can capture and secure the foreign body FB. After the foreign body FB is captured by the loop 174 of the snare 170, the snare loading device 100*d* can be decoupled from the handle 400, and the handle 400 together with the snare 170 can be pulled back or in the proximal direction, thereby securing the foreign body FB against the catheter tube 200 (FIG. 5H). Thereafter, the lock 220*d* can clamp or secure the snare 170 relative to the snare loading device 100*d* (FIG. 5I), as described above. For instance, the lock 220*d* can move in the proximal direction, thereby rotating the cam 370*d* downward and locking the wire 172 of the snare within the main channel 150*d* of the snare loading device 100*d*.

Accordingly, the captured foreign body FB can be locked between or within the loop 174 of the snare 170 and between the catheter tube 200 and can be secured by the snare loading device 100*d*, which can hold the snare 170 locked relative to the catheter tube 200. Specifically, the snare loading device 100*d* can remain coupled to the luer 202 and, thus, can remain stationary relative to the catheter tube 200. As the lock 220*d* locks the snare 170 relative to the snare loading device 100*d*, the snare 170 also can remain in a fixed position relative to the catheter tube 200, and can, therefore, secure the foreign body FB relative to the catheter tube 200. Subsequently, the snare loading device 100*d* together with the catheter tube 200 and the foreign body FB can be safely removed from the patient's body.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A snare loading device for loading a snare having a wire, the snare loading device comprising:
    a main body comprising a distal opening and a proximal opening, wherein the proximal opening is configured to permit entry of a distal end of the snare through the proximal opening into the main body;
    a main channel located in the main body and extending between the distal opening and the proximal opening, the main channel being sized and configured to accept the snare such that the snare extends across an entirety of the main body;
    a collapsing taper located in the main body and near a proximal end thereof, the collapsing taper being connected to or merging with the main channel;
    a cam disposed completely within the main body and rotatably coupled to the main body;
    a lock slidably coupled to the main body, wherein the lock is configured to transfer a force exerted directly by a user on the lock to push the cam, thereby causing the cam to rotate toward and engage the wire of the snare; and
    a handle configured to axially translate the snare and to couple to the main body,
    wherein the cam comprises a flat angled surface on top of the cam configured to interface with the lock in a manner that rotates the cam, thereby locking the snare in the main channel, and wherein the flat angled surface extends from a distal end of the cam toward a proximal end of the cam.

2. The snare loading device as recited in claim 1, wherein:
    the main channel comprises a locking portion; and
    the cam is positioned in a manner that rotation of the cam clamps the snare in the locking portion of the main channel.

3. The snare loading device as recited in claim 2, wherein the locking portion has a curvilinear shape that curves away from the cam such that the curvilinear shape of the locking portion provides a concave surface for interaction with the snare.

4. The snare loading device as recited in claim 3, wherein the cam comprises a locking bottom portion that has a convex surface.

5. The snare loading device as recited in claim 1, wherein the main channel has a curvilinear configuration.

6. The snare loading device as recited in claim 1, wherein the main body further comprises a tip on a distal end thereof, the tip being sized and configured to couple to a luer.

7. A snare loading device for loading a snare having a loop and a wire, the snare loading device comprising:
    a main body comprising a distal opening and a proximal opening, wherein the proximal opening is configured to permit entry of a distal end of the snare through the proximal opening into the main body;
    a main channel located in the main body, the main channel being sized and configured to accept the wire of the snare such that the wire extends across an entirety of the main body, the main channel defining the distal opening and the proximal opening, the distal opening being configured to compress the loop of the snare;
    a cam disposed completely within the main body and directly rotatably coupled to the main body;
    a lock slidably secured to the main body, the lock, configured transfer a force exerted directly by a user on the lock to push the cam such that the cam rotates and engages the wire of the snare, wherein the entire lock slides along the main body; and
    a handle configured to axially translate the snare and to couple to the main body.

8. The snare loading device as recited in claim 7, wherein the main body further comprises one or more closure locks and corresponding one or more locking sections configured to secure a left half and a right half together.

9. The snare loading device as recited in claim 8, wherein the one or more closure locks and the corresponding one or more locking sections form an interference lock therebetween.

10. The snare loading device as recited in claim 7, wherein the main body has a tip on the distal end thereof, the tip being sized and configured to fit into one or more of a catheter tube and a luer.

11. The snare loading device as recited in claim 10, wherein the distal opening has an inward curve.

12. The snare loading device as recited in claim 7, wherein the main channel is defined by and disposed between a left half of the main body and a right half of the main body, wherein the left half of the main body and the right half of the main body are separate and distinct components that are secured to one another.

13. The snare loading device as recited in claim 12, wherein:

the main body further comprises one or more of the distal locking tabs and proximal locking tabs; and the lock is configured to slide over the one or more of distal locking tabs and proximal locking tabs to secure the left half of the main body and the right half of the main body together.

14. A snare loading device for loading a snare having a wire, the snare loading device comprising:

a main body comprising a distal opening and a proximal opening, wherein the proximal opening is configured to permit entry of a distal end of the snare through the proximal opening into the main body;

a main channel located in the main body and extending between the distal opening and the proximal opening, the main channel being sized and configured to accept the snare such that the snare extends across an entirety of the main body;

a collapsing taper located in the main body and near a proximal end thereof, the collapsing taper being connected to or merging with the main channel;

a cam disposed completely within the main body and rotatably coupled to the main body;

a lock slidably coupled to the main body, wherein the lock is configured to transfer a force exerted directly by a user on the lock to push the cam, thereby causing the cam to rotate toward and engage the wire of the snare;

a handle configured to axially translate the snare and to couple to the main body, wherein the cam comprises a flat angled surface on top of the cam and the cam is disposed above the main channel, and wherein the flat angled surface extends from a distal end of the cam toward a proximal end of the cam.

* * * * *